(12) United States Patent
Itonaga et al.

(10) Patent No.: US 6,336,901 B1
(45) Date of Patent: Jan. 8, 2002

(54) SPHYGMOMANOMETER CUFF ACHIEVING PRECISE MEASUREMENT OF BLOOD PRESSURE

(75) Inventors: Kazunobu Itonaga; Hiroyuki Kato; Takahide Tanaka; Hironori Sato, all of Kyoto (JP)

(73) Assignee: Omron Corporation, Tokyo (JP)

( * ) Notice: Subject to any disclaimer, the term of this patent is extended or adjusted under 35 U.S.C. 154(b) by 0 days.

(21) Appl. No.: 09/502,021

(22) Filed: Feb. 11, 2000

Related U.S. Application Data

(63) Continuation-in-part of application No. PCT/JP99/02208, filed on Apr. 26, 1999.

(30) Foreign Application Priority Data

Apr. 27, 1998 (JP) .......................................... 10-116928
Feb. 12, 1999 (JP) ............................................. 11-33860

(51) Int. Cl.[7] .................................................. A61B 5/00
(52) U.S. Cl. ...................................... 600/499; 606/202
(58) Field of Search ................................ 600/490, 499; 606/202

(56) References Cited

U.S. PATENT DOCUMENTS

| | | | | |
|---|---|---|---|---|
| 4,210,154 A | * | 7/1980 | Klein | 600/499 |
| 4,920,971 A | * | 5/1990 | Blessinger | 600/499 |
| 4,938,226 A | * | 7/1990 | Danielsson et al. | 600/499 |
| 5,069,219 A | * | 12/1991 | Knoblich | 600/499 |
| 5,388,585 A | * | 2/1995 | Tomita | 600/494 |

FOREIGN PATENT DOCUMENTS

| | | |
|---|---|---|
| JP | 62-116703 | 7/1987 |
| JP | 03280931 | 12/1991 |
| JP | 05-269089 | 10/1993 |
| JP | 6-28636 | 4/1994 |
| JP | 7-24304 | 5/1995 |
| JP | PCT/JP99/02208 | 4/1999 |

OTHER PUBLICATIONS

Copy of International Search Report dated Aug. 31, 1999 issued in PCT/JP99/02208.

* cited by examiner

Primary Examiner—Robert L. Nasser
(74) Attorney, Agent, or Firm—Morrison & Foerster LLP

(57) ABSTRACT

A cuff for a sphygmomanometer is constituted of an air bag for pressurization into which a predetermined amount of air is supplied and connected to a pressure sensor, an air bag for press into which a predetermined amount of fluid is supplied for causing the pressurization air bag to press the artery in the wrist portion, and a band for attaching both air bags to the wrist portion. When blood pressure is to be measured, a predetermined amount of air is supplied into the pressurization air bag and then air is supplied into the press air bag. The press air bag is accordingly expanded to cause the pressurization air bag to pressurize the artery. In this way, the sphygmomanometer cuff is provided which can overcome discomfort due to a feeling of being overly pressurized or dampness and ensure blocking of the blood flow in the artery so as to achieve measurement with higher precision.

13 Claims, 19 Drawing Sheets

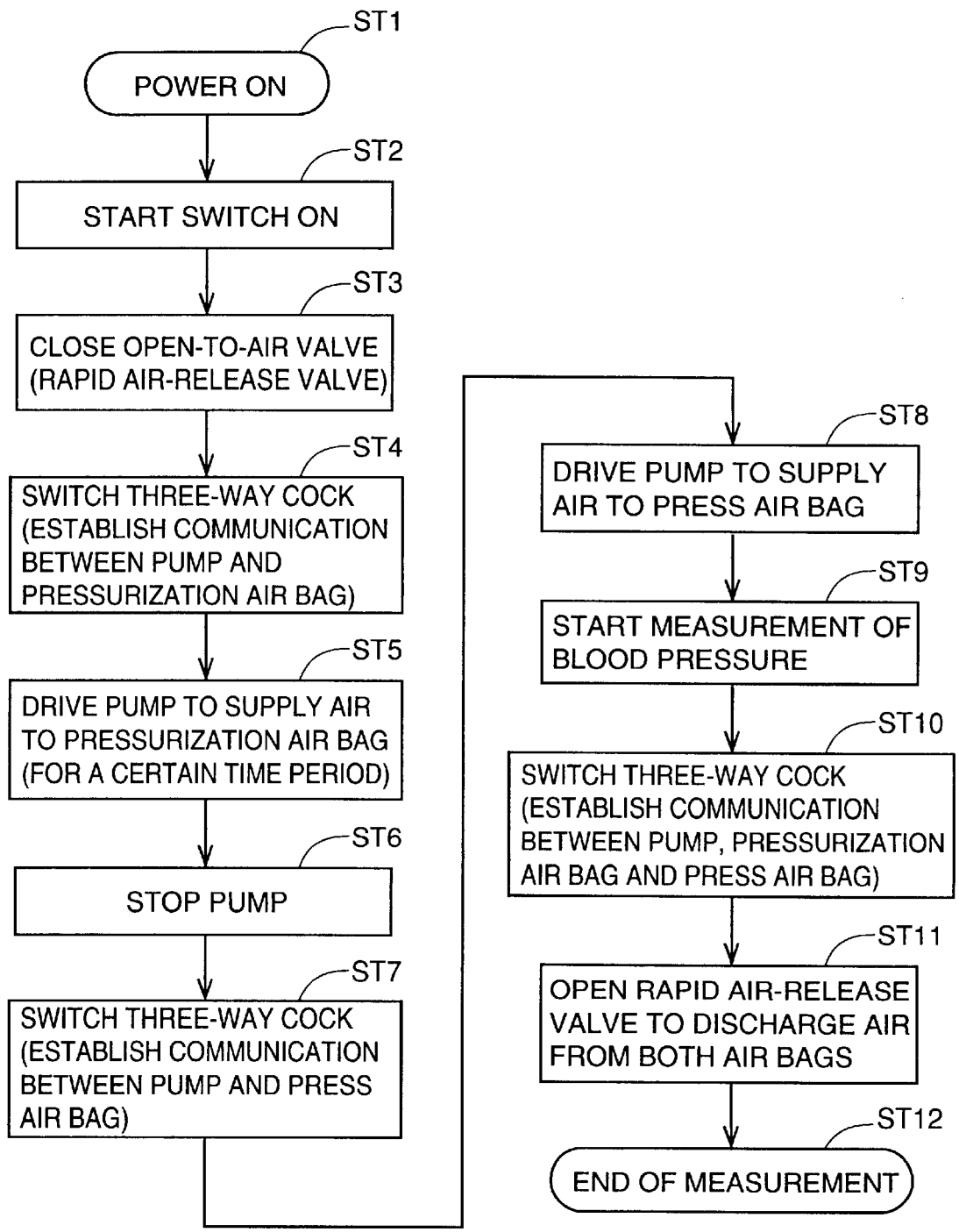

CIRCUMFERENTIAL DIRECTION OF WRIST

AXIAL DIRECTION OF WRIST

AXIAL DIRECTION OF WRIST

AXIAL DIRECTION OF WRIST

AXIAL DIRECTION OF WRIST

AXIAL DIRECTION OF WRIST 100

AXIAL DIRECTION OF WRIST

SPHYGMOMANOMETER CUFF ACHIEVING PRECISE MEASUREMENT OF BLOOD PRESSURE

REFERENCE TO RELATED APPLICATION

This application is a continuation-in-part of International Application No. PCT/JP99/02208, filed Apr. 26, 1999.

BACKGROUND OF THE INVENTION

1. Field of the Invention

The present invention relates to a blood pressure cuff for a sphygmomanometer that is used by being attached to some region of a living body or subject for measuring blood pressure. In particular, the invention relates to a cuff most appropriate for a wrist sphygmomanometer for measuring blood pressure at the wrist portion.

2. Description of the Background Art

FIGS. 9A and 9B illustrate a conventional sphygmomanometer cuff. As shown in FIGS. 9A and 9B, the conventional sphygmomanometer cuff 70 is constituted of an air bag 71 into which air is supplied and a strip-like band 72 for attaching air bag 71 to a certain region (arm, wrist) 80 of a living body or subject. Band 72 of cuff 70 is used to attach air bag 71 to subject region 80 and then air is supplied to air bag 71, so that an artery 81 of subject region 80 is pressurized and accordingly blood pressure is measured during the process of discharging air from air bag 71.

Japanese Patent Publication No. 6-28636 (Japanese Patent Laying-Open No. 63-147434) discloses "Sphygmomanometer Arm Band and Sphygmomanometer Pressurizing Device" as a prior art of the sphygmomanometer cuff. The sphygmomanometer arm band includes, in addition to a main body of the arm band, an inflatable bag and connecting means, an actuator for decreasing the diameter of the arm band by shortening the length of the arm band body. Regarding this arm band, the actuator is inflated before expansion of the inflatable bag and thus the arm band body is tighten up to an extent which is sufficient to measure blood pressure. The inflatable bag is thereafter distended to have a pressure sufficiently higher than the maximum blood pressure and then the air within the inflatable bag is gradually discharged. Blood pressure is thus measured during the discharging process.

In conventional cuff 70, the pressurizing force required to block the flow of blood in artery 81 is provided by the volume of expansion of air bag 71 only. If cuff 70 is closely attached to subject region 80 as shown in FIG. 9A, air bag 71 has a wide flat portion (effective range). When air bag 71 is distended in this state, the pressurizing force is conveyed to artery 81 which is enough to block the flow of blood in artery 81. On the other hand, if cuff 70 is attached loosely to subject region 80 as shown in FIG. 9B, air bag 71 has a relatively narrow effective range. Therefore, even if air bag 71 is inflated sufficiently in this state, the pressurizing force is not conveyed to artery 81 and accordingly the flow of blood in artery 81 is not blocked. In this case, an additional volume of expansion of air bag 71 is required corresponding to the space between air bag 71 and the skin, resulting in a measurement higher than a true value.

In order to avoid this problem, cuff 70 should be closely fit onto subject region 80 as shown in FIG. 9A. However, if cuff 70 stands being attached closely to subject region 80 all the time, there would arise a feeling of being excessively pressurized. Especially in the period of sweaty summer or rainy season, there would arise discomfort. The resultant problem is difficulty in constant attachment of the sphygmomanometer (particularly wrist sphygmomanometer) even if the sphygmomanometer body or cuff is reduced in size.

Regarding the arm band and pressurizing device disclosed in the patent above, the actuator operates to reduce the diameter of the arm band and the arm band is then closely attached to the subject in a manner similar to the conventional wrapping state, and the operation of the actuator is cancelled to allow the diameter of the arm band to increase and thus loosen the arm band. This approach advantageously achieves the effect of avoiding the discomfort caused by the feeling of being excessively pressurized and unpleasant dampness. However, in measurement of blood pressure, the actuator is first expanded to pull and accordingly tighten the arm band body and then the inflatable bag is distended until a predetermined pressure is obtained. Therefore, the inflatable bag is likely to be shifted from its original position. In other words, the possibility of the shift of the inflatable bag is higher when the actuator operates to pull the arm band body after the arm band is loosely attached at first. In the event of the shift of the inflatable bag, a sufficient degree of pressurizing force cannot be conveyed to the artery, resulting in the state shown in FIG. 9B. If the blood flow in the artery is to be blocked in this state, the volume of expansion of the inflatable bag must be increased, causing further discomfort such as the feeling of excessive pressurization.

SUMMARY OF THE INVENTION

One object of the present invention is to provide a sphygmomanometer cuff which can ensure blocking of the blood flow in an artery so as to obtain measurements with higher precision.

Another object of the present invention is to provide a sphygmomanometer cuff capable of eliminating discomfort caused by the feeling of being excessively pressurized, dampness and the like.

Still another object of the present invention is to provide a sphygmomanometer cuff having a pressurization surface ensuring pressurization of a particular region of a living subject.

Those objects of the present invention can be accomplished by a sphygmomanometer cuff which includes the following components. Specifically, a sphygmomanometer cuff according to one aspect of the present invention includes a fluid bag for pressurization into or in which a predetermined amount of fluid is supplied or confined and to which a pressure sensor is connected, a press portion into which a predetermined amount of fluid is supplied to cause the pressurization fluid bag to press a region of a living subject, and an attachment unit for attaching the pressurization fluid bag and the press portion to the subject region.

The pressurization fluid bag of the cuff having the pressure sensor connected thereto is different from the conventional cuff and the inflatable bag disclosed in the patent above in that only a predetermined amount of fluid is supplied into the fluid bag or a predetermined amount of fluid is confined therein in advance and then the press portion causes the pressurization fluid bag to press the subject region. In measurement of blood pressure, the press portion may just be used to press the pressurization fluid bag against the subject region. Therefore, the cuff may be attached loosely to the subject region and accordingly the discomfort caused by the feeling of excess pressure and dampness can be avoided so as to enable the cuff to be attached all the time. Further, only a predetermined amount of fluid is supplied into or confined in the pressurization fluid bag, and the force for sufficiently pressurizing the subject region by the pressurization fluid bag is obtained by the press portion. Specifically, the press portion causes the pressurization fluid bag to press the subject region. By positioning the pressurization fluid bag at a predetermined site (where artery is pressurized) when the cuff is attached, even if the cuff is attached loosely, it is possible to prevent shift of the position of the pressurization fluid bag due to the operation of the press portion which hinders conveyance of a sufficient pressure to the artery. Measurements with higher precision can thus be obtained.

According to another aspect of the invention, a sphygmomanometer cuff includes a fluid bag for pressurization into or in which a predetermined amount of fluid is supplied or confined and which is connected to a pressure sensor, a press unit into which a predetermined amount of fluid is supplied for causing the pressurization fluid bag to press the subject region, and an attachment unit for attaching the pressurization fluid bag and the press unit to the subject region. The pressurization fluid bag is curved along the surface of the subject region. The pressurization fluid bag fits onto the surface of the subject region without gap, so that the pressure on the artery can correctly be detected and accordingly the blood pressure can be measured with high precision.

The pressurization fluid bag may be divided into small parts which are placed in the circumferential direction of the subject region. The pressurization fluid bag is thus composed of a plurality of small bags, not of one bag, so as to improve fitness onto the surface of the subject region and accordingly achieve correct measurement of the pressure on the artery.

The pressurization fluid bag may have a wavelike structure with projection and depression extending in the axial direction of the subject region. Even if the pressurization fluid bag is partially caught by tendon or bone in the subject region when the pressure is exerted, the wavelike structure allows the remaining part to move in the pressurized direction regardless of the caught portion, so that the pressure on the artery can correctly be detected.

The pressurization fluid bag may have a portion extending in the axial direction of the subject region that has a hardness different from that of the remaining portion. The portion of the pressurization fluid bag to be associated with the tendon and bone in the subject region may have a hardness lower than that of the remaining portion so that the portion associated with the tendon and bone is easily compressed and the remaining portion moves in the pressurized direction regardless thereof. In this way, the pressure on the artery can correctly be detected.

The pressurization fluid bag includes a pressurization surface which is more elastic than the subject region and includes a portion having a compression displacement relative to the pressure from the subject region smaller than compression displacement of fluid inside the pressurization surface. Here, the compression displacement means a displacement caused by compression due to the pressure from the subject region. When pressure is exerted, the pressurization surface is pushed by the subject region to be displaced inwardly, while the remaining portion is hardly displaced. Consequently, the internal pressure of the pressurization fluid bag becomes almost equal to the pressure on the artery and thus correct detection of the pressure on the artery is possible.

According to still another aspect of the invention, the press unit of the sphygmomanometer cuff is arranged opposite to the pressurization surface of the pressurization fluid bag and is a fluid bag for press which expands and contracts upon supply and discharge of fluid. The pressurization fluid bag has a restraint tool placed opposite to the pressurization surface for restraining the press fluid bag from swelling in the axial direction of the subject region. When the press fluid bag is expanded, the press fluid bag is prevented by the restraint tool from swelling in the axial direction of the subject region. Therefore, the pressing force generated by expansion of the press fluid bag is efficiently transmitted to the pressurization fluid bag, so that the transmission efficiency of the pressurization force is enhanced.

According to a further aspect of the invention, the pressurization fluid bag of the sphygmomanometer cuff has a pressurization surface which is less elastic than the subject region and has a portion having a compression displacement relative to the pressure from the subject region that is greater than compression displacement of fluid inside the pressurization surface. When pressure is exerted, the pressurization surface is hardly displaced, while the remaining portion is displaced according to the pressurization force. As a result, a uniform distribution of the pressurization force is established over the pressurization surface of the pressurization fluid bag. In other words, the pressurization force is uniform regardless of the position of the pressurization surface, and thus the pressure on the artery can be measured correctly.

According to a further aspect of the invention, the sphygmomanometer cuff includes a cover for preventing the pressurization fluid bag, when the cuff is attached to the subject region, from being subjected to pressure from the subject region or any external pressure. As the pressurization fluid bag is not subjected to the pressure from the subject region or external pressure owing to the cover upon attachment, zero point of the pressure can precisely be adjusted with the cuff attached as it is whereby a correct measurement of the blood pressure is possible.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 8 is a flow chart illustrating an overall operation of a sphygmomanometer having the fluid system in FIG. 6 with the three-way cock in FIGS. 7A to 7C.

DESCRIPTION OF THE PREFERRED EMBODIMENTS

The present invention is hereinafter described in conjunction with the embodiments thereof.

First Embodiment

Figure 1:
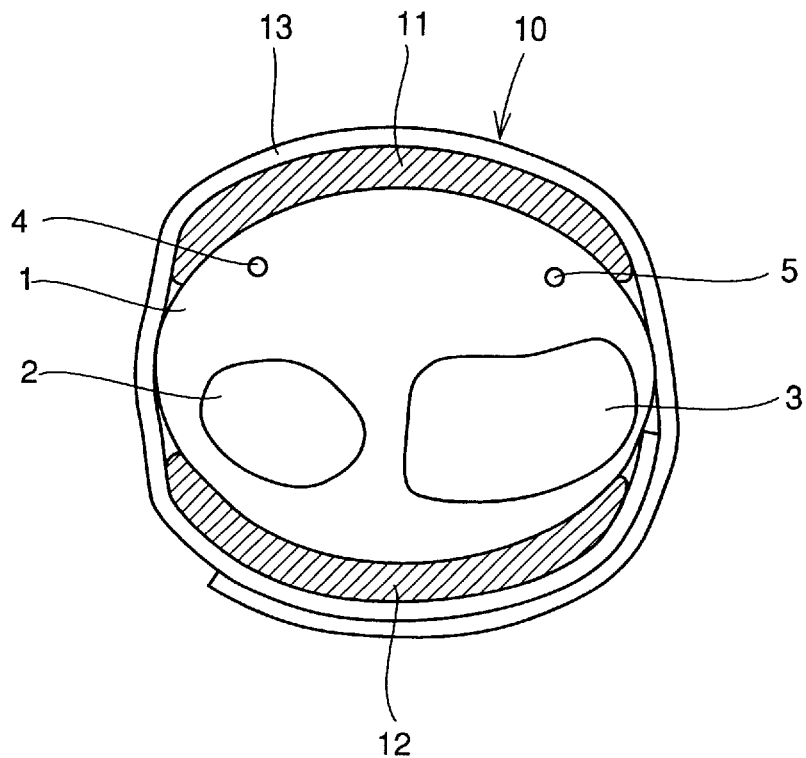
FIG. 1 is a cross sectional view illustrating a main portion of a cuff which is attached to the wrist portion in one embodiment of the invention.

Referring to FIG. 1, a cuff 10 used for a wrist sphygmomanometer is constituted of an air bag for pressurization (pressurization fluid bag) 11 into which a predetermined amount of air is supplied so as to pressurize arteries 4 and 5 of a subject region (wrist portion) 1, an air bag for press (press fluid bag) 12 serving as a pressing section to cause pressurization air bag 11 to press wrist portion 1, and a strip-like band 13 serving as an attachment unit for attaching both air bags 11 and 12 to wrist portion 1. Pressurization air bag 11 and press air bag 12 of cuff 10 have respective widths almost equal to the transverse width of wrist portion 1. The bags are located opposite to each other with wrist portion 1 therebetween, and cuff 10 is attached to wrist portion 1 such that pressurization air bag 11 faces the inside of wrist portion 1. Band 13 has a hook-and-loop fastener so as to fix the wrapping state at an arbitrary position.

Cuff 10 is attached to wrist portion 1 as shown in FIG. 1. Specifically, cuff 10 is wrapped around wrist portion 1 by band 13 such that pressurization air bag 11 faces an ulnar artery 4 and a radial artery 5 while press air bag 12 faces the opposite side (an ulna 2 and a radius 3). It is noted that ulna 2 and ulnar artery 4 are located on the little finger side of the hand and radius 3 and radial artery 5 are located on the thumb side in human wrist portion 1. It is unnecessary to tightly wrap cuff 10 around wrist portion 1 and the cuff may be wrapped loosely to an extent which is enough to prevent pressurization air bag 11 from shifting from the position facing arteries 4 and 5.

When blood pressure is to be measured, pressurization air bag 11 is first supplied with a predetermined amount of air and accordingly inflated. The amount of air to be supplied is not specified uniquely, however, the amount thereof should be enough to expand air bag 11 over the entire surface maintaining substantially flat shape when air is supplied before attachment of the cuff to the wrist portion.

Next, press air bag 12 is supplied with air and is thus inflated, causing pressurization air bag 11 to press wrist portion 1 (arteries 4 and 5). The air is supplied into air bag 12 until a predetermined pressure (pressure higher than the maximum blood pressure) is achieved. When the expansion of air bag 12 causes the pressurization force (internal pressure) of air bag 11 to reach the predetermined pressure, supply of air into air bag 12 is stopped. After this, the air within air bag 12 is gradually discharged and the blood pressure is measured during the process of discharge. After the measurement of blood pressure is completed, the air in air bag 11 is also discharged.

Pressurization air bag 11 of cuff 10 above is supplied with only a predetermined amount of air and accordingly air bag 11 does not exceed a predetermined degree of expansion. Air bag 11 is then pressed inwardly toward wrist portion 1 by the expansion of air bag 12. Consequently, even if cuff 10 is attached to wrist portion 1 by band 13 to meet the tightness according to the user's preference, air bag 11 is never shifted from its original position and the width of air bag 11 does't change. Therefore, the flow of blood in arteries 4 and 5 (especially radial artery 5) is blocked surely by air bag 11 and the resultant measurement of the blood pressure does not exceed a real value, achieving a measurement with higher precision. In other words, cuff 10 may be attached all the time by loosely wrapping it like a wrist watch, re-wrapping of cuff 10 to closely fit it onto the wrist for each measurement of blood pressure is unnecessary and thus the loose-fit state may be maintained to make measurement. Further, cuff 10 may be loosely wrapped when attached, eliminating discomfort such as the feeling of excessively pressurized, unpleasant dampness and the like.

Figure 3:
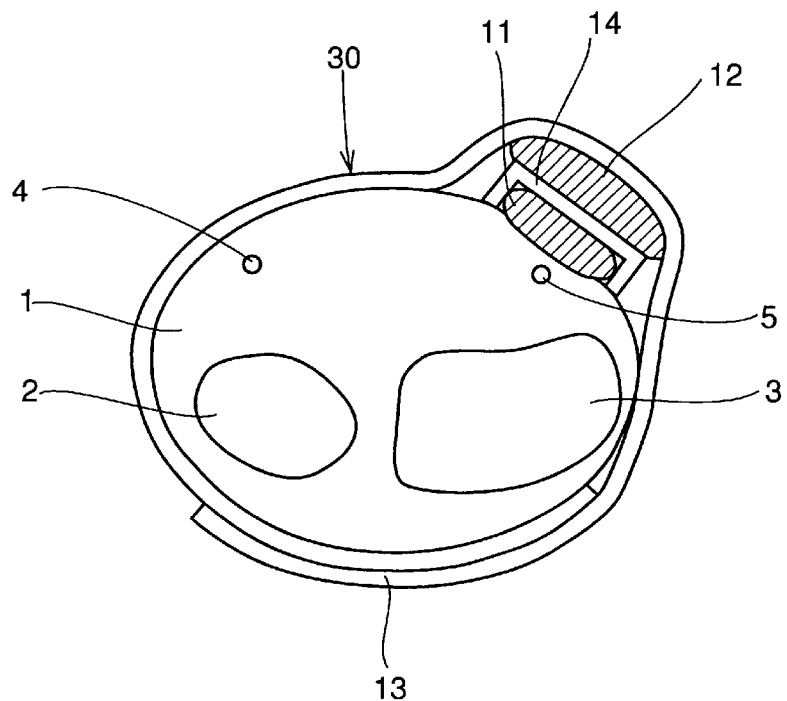
FIG. 3 is a cross sectional view illustrating a main portion of a cuff attached to the wrist portion in still another embodiment of the invention.
Figure 4:
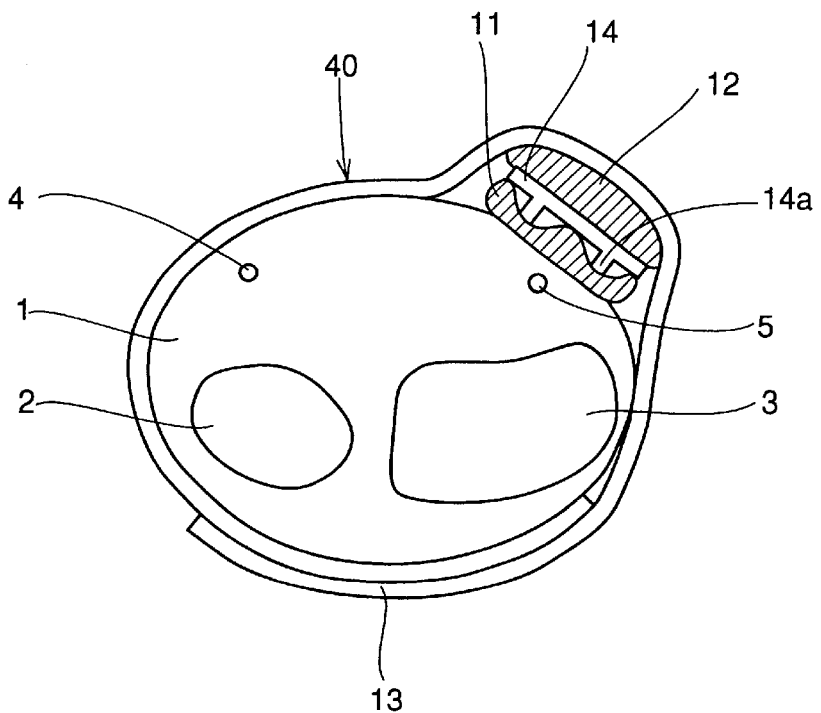
FIG. 4 is a cross sectional view illustrating a main portion of a modification of the cuff.

It is noted that the widths of pressurization air bag 11 and press air bag 12 (widths in the transverse direction of wrist portion 1) are almost equal to the width of wrist portion 1, however, especially air bag 11 may have a narrower width as shown in FIGS. 3 and 4 which is enough to pressurize only radial artery 5. Further, the method of supplying a predetermined amount of air into air bag 11 may appropriately be selected from a method of supplying air by a manual pump at a certain number of times, a method of supplying air by an electric pump at a certain voltage or for a certain period of time, a method of confining a certain amount of air in advance, and the like. In addition, measurement of the blood pressure may be started any time among the start of the supply of a predetermined amount of air to air bag 11, during the period of the supply, after the supply and the like.

Second Embodiment

Figure 2:
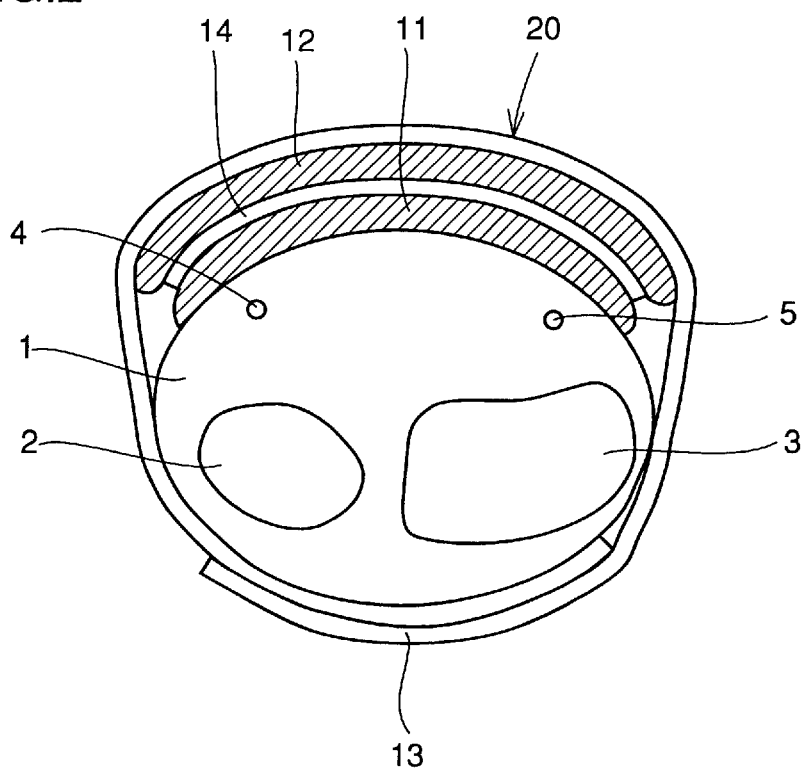
FIG. 2 is a cross sectional view illustrating a main portion of a cuff attached to the wrist portion in another embodiment of the invention.

FIG. 2 is a cross sectional view of a main portion of a sphygmomanometer cuff which is attached to the wrist portion in the second embodiment. The components of the second embodiment corresponding to those of the first embodiment are denoted by the same reference characters. Cuff 20 has a press section for causing a pressurization air bag 11 to press wrist portion 1, the press portion consisting of an intervening member 14 placed on the outside of pressurization air bag 11, and a press air bag 12 placed on the outside of intervening member 14. Intervening member 14 holds air bag 11 while it allows the pressure in air bag 12 to be exerted uniformly on air bag 11 and has a width almost equal to the width of air bag 11. It is noted that intervening member 14 may be formed of a sheet material having an appropriate flexibility, rubber or sponge, or inflexible materials.

Press air bag 12 of cuff 20 is inflated and the pressurizing force thereof is conveyed via intervening member 14 to pressurization air bag 11, so that pressurization air bag 11 pressurizes arteries 4 and 5 to achieve the effects discussed above.

A cuff in another embodiment is shown in FIG. 3. A pressurization air bag 11 of cuff 30 has a minimum size (width) required for pressurizing only a radial artery 5. Pressurization air bag 11 is housed in an intervening member 14 and a press air bag 12 has a minimum size required to press the back of intervening member 14.

Cuff 30 is loosely wrapped around a wrist portion 1 such that pressurization air bag 11 faces radial artery 5 upon attachment. When blood pressure is to be measured, a predetermined amount of air is supplied into air bag 11 and thereafter air is supplied into air bag 12 so as to inflate air bag 12 and thus cause air bag 11 to pressurize artery 5. Since air bag 11 is positioned by intervening member 14 relative to artery 5, air bag 11 is never shifted from its original position even if the size thereof is small.

FIG. 4 illustrates a modification of cuff 30 in FIG. 3. A cuff 40 in FIG. 4 includes an intervening member 14 which has a leg portion 14a. Two linear leg portions 14a may be placed in parallel, or annular leg portion 14a may be placed. Leg portion 14a of intervening member 14 of cuff 40 surely positions air bag 11 relative to artery 5.

Third Embodiment

Figure 5:
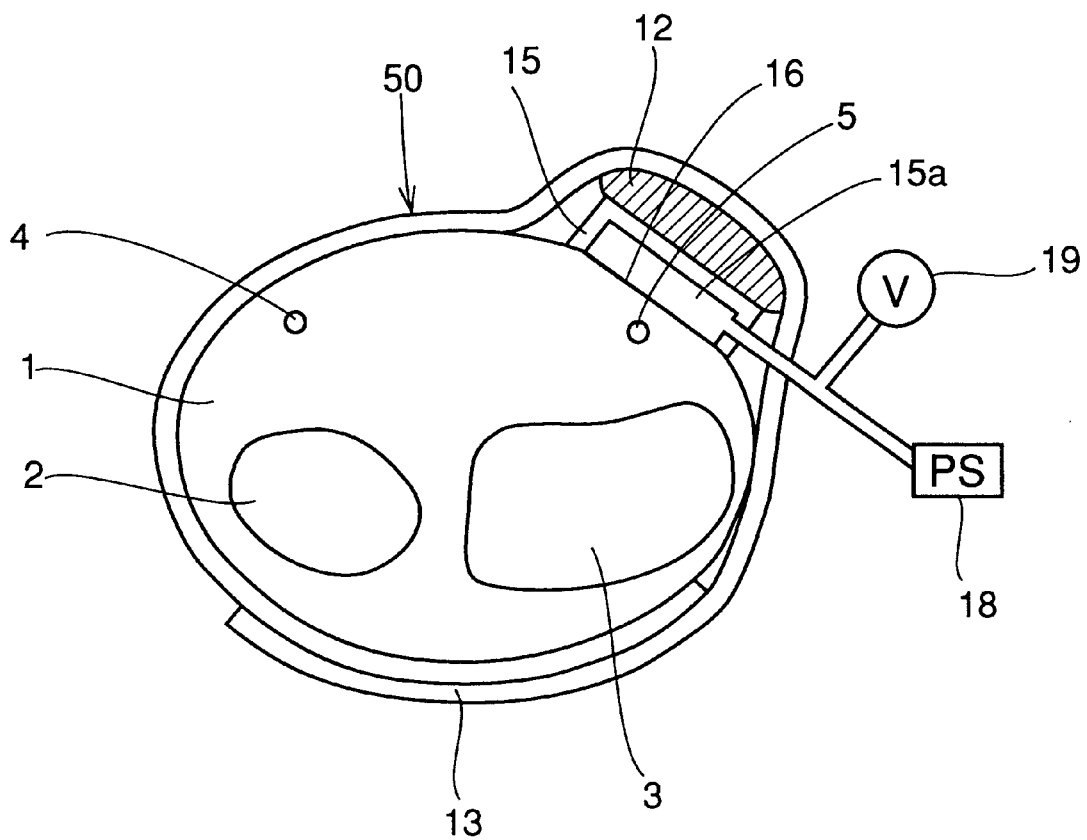
FIG. 5 is a cross sectional view illustrating a main portion of a cuff attached to the wrist portion in a further embodiment of the invention.

A cuff in the third embodiment is shown in FIG. 5. A pressurization fluid bag of cuff 50 consists of an air introduction member (fluid introduction member) 15 having a space 15a into which air is supplied, and a press film 16 attached to air introduction member 15 to seal space 15a.

Space 15a of air introduction member 15 is connected to a pressure sensor 18 through a flow path (e.g. tube), and an open-to-air valve 19 is provided on the way through the flow path.

When blood pressure is not measured, valve 19 of cuff 50 is opened so as to open space 15a of air introduction member 15. When measurement of the blood pressure is to be done, valve 19 is closed and the internal pressure of space 15a is detected by pressure sensor 18 while air is supplied into space 15a until the internal pressure reaches a predetermined pressure. Then, press film 16 bulges to moderately press a wrist portion 1. Air is thereafter supplied into an air bag 12 to inflate air bag 12 so as to press air introduction member 15 by the inflation of air bag 12 and accordingly cause press film 16 to pressurize an artery 5.

The following is another operation manner. When blood pressure is to be measured, valve 19 is closed and the internal pressure of space 15a is detected by pressure sensor 18. With a predetermined amount of air confined in space 15a, air may be supplied into air bag 12 to press air introduction member 15 by expansion of air bag 12 and accordingly cause press film 16 to pressurize artery 5.

Figure 6:
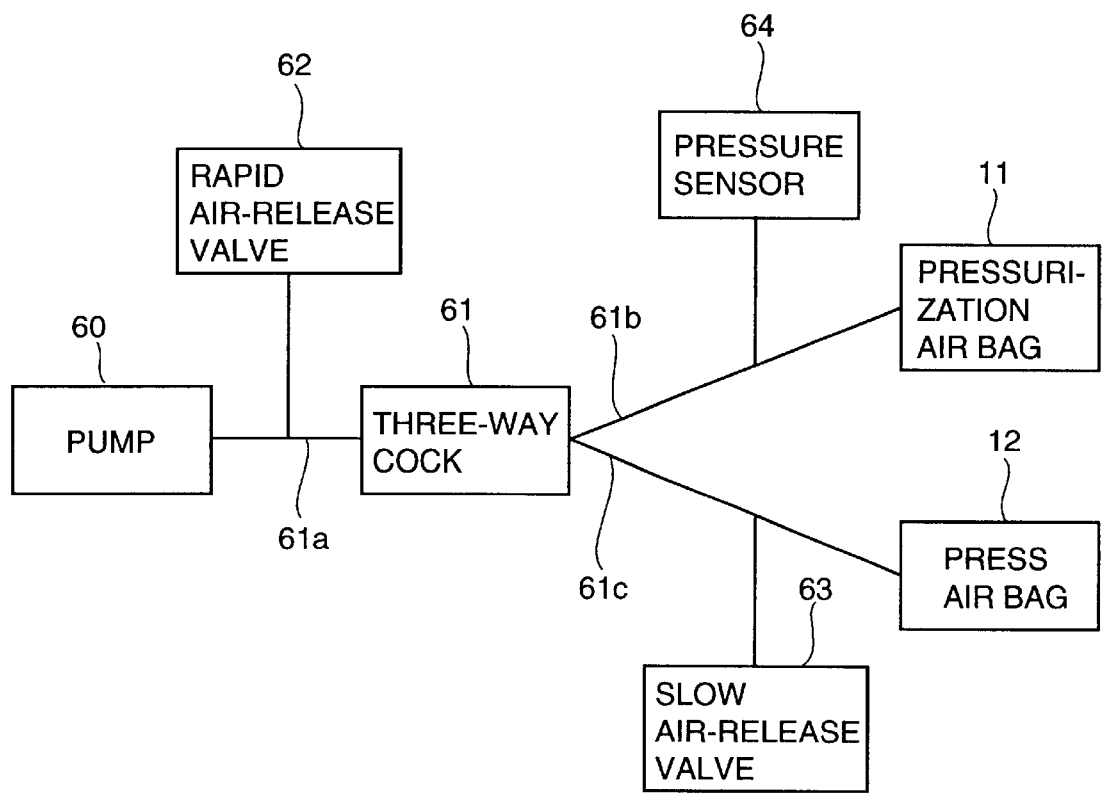
FIG. 6 is a block diagram illustrating a structure of a fluid system in a sphygmomanometer having any of the cuffs shown in FIGS. 1 to 4.

FIG. 6 is a block diagram illustrating a structure of a fluid system associated with pressurization air bag 11 and press air bag 12 in any of cuffs 10, 20, 30 and 40 illustrated respectively in FIGS. 1 to 4. In this fluid system structure, pressurization air bag 11 and press air bag 12 are connected to a pump 60 for an air supply source via a three-way cock 61. Further, a rapid air-release valve 62 is connected to a flow path 61a between pump 60 and three-way cock 61, a slow air-release valve 63 is connected to a flow path 61c between three-way cock 61 and press air bag 12, and a pressure sensor 64 is connected to a flow path 61b between three-way cock 61 and pressurization air bag 11.

Figure 7A:
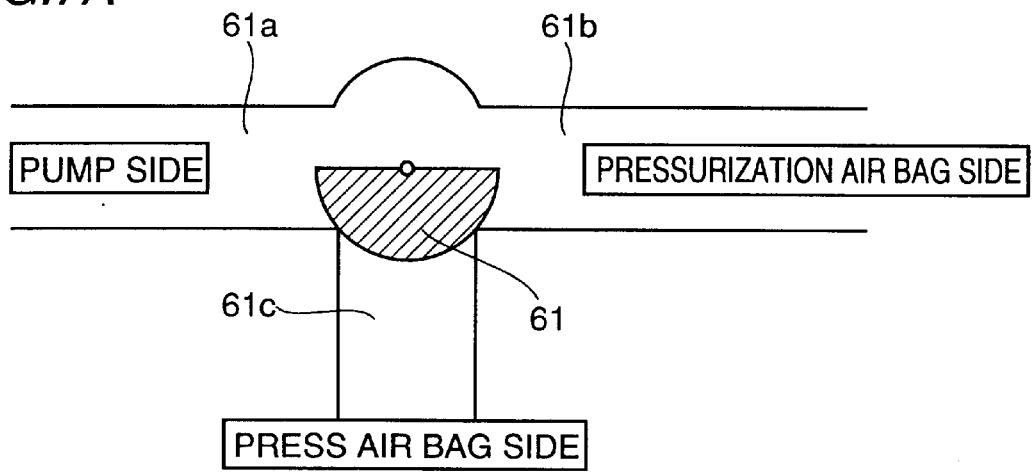
FIGS. 7A to 7C generally illustrate a structure and function of a three-way cock employed in the fluid system shown in FIG. 6.
Figure 7B:
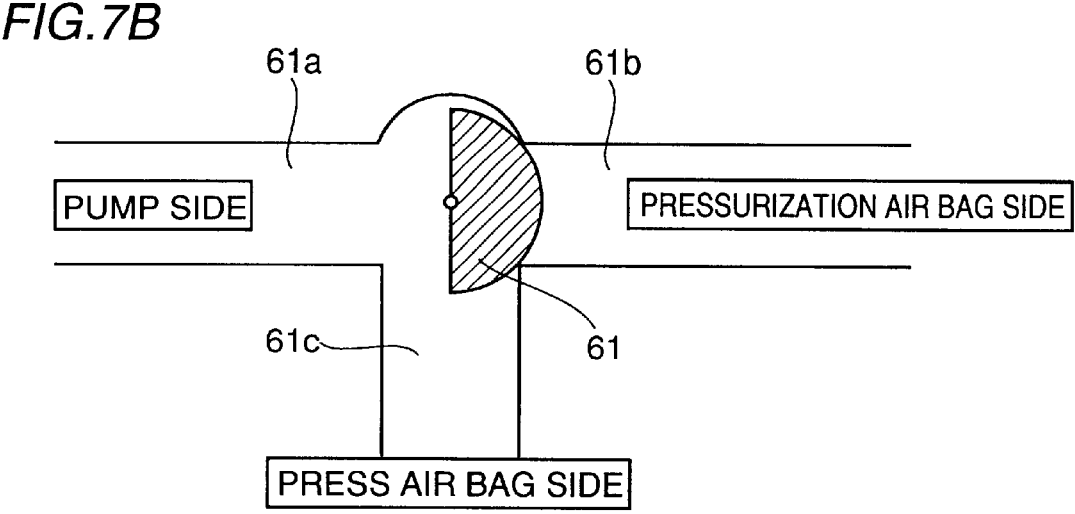
Figure 7C:
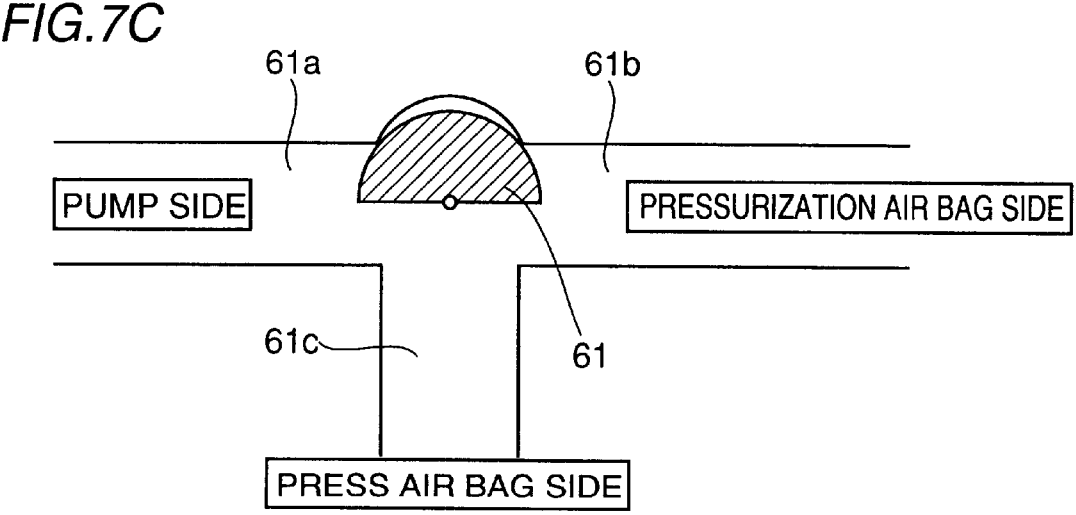
Figure 9A:
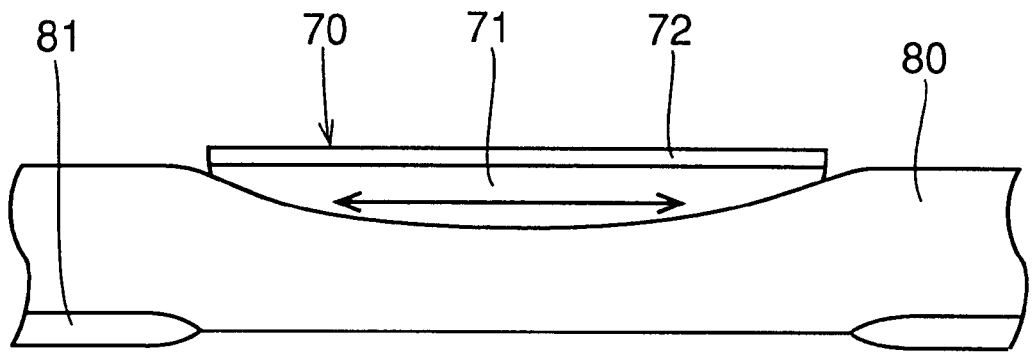
FIG. 9A is a cross sectional view illustrating a function of a conventional cuff which is attached closely to a subject region and FIG. 9B is a cross sectional view illustrating a function thereof which is attached loosely to the subject region.
Figure 9B:
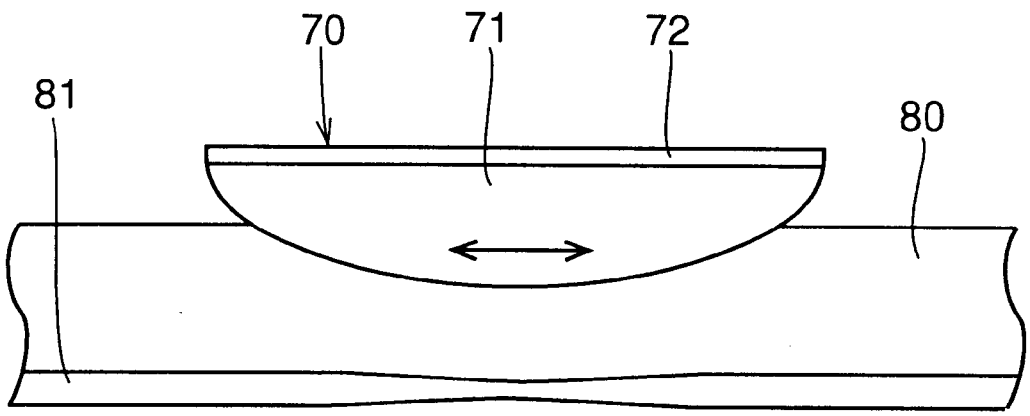

Three-way cock 61 having the structure and function generally illustrated in FIGS. 7A to 7C establishes communication between two or all of the three flow paths, i.e. flow path 61a associated with pump 60, flow path 61b associated with pressurization air bag 11, and flow path 61c associated with press air bag 12. When there is established communication between flow paths 61a and 61b and flow path 61c is closed as shown in FIG. 7A, air is supplied from pump 60 to pressurization air bag 11 only. When communication is established between flow paths 61a and 61c and flow path 61b is closed as shown in FIG. 7B, air from pump 60 is supplied to press air bag 12 only. When communication is established between three flow paths 61a , 61b and 61c as shown in FIG. 7C, air from pump 60 is supplied to both of pressurization air bag 11 and press air bag 12.

Referring to the flow chart shown in FIG. 8, an overall operation of a sphygmomanometer (wrist sphygmomanometer) having the fluid system in FIG. 6 with three-way cock 61 of the structure shown in FIGS. 7A to 7C is now described. The power of the sphygmomanometer is first turned on (step 1, hereinafter abbreviated as ST1), then a start switch is turned on (ST2), and rapid air-release valve (open-to-air valve) 62 is accordingly closed (ST3). Next, three-way cock 61 switches to the state in FIG. 7A to allow pump 60 and pressurization air bag 11 to communicate with each other (ST4).

Next, pump 60 operates to supply air into pressurization air bag 11 for a certain period of time (by a predetermined amount) (ST5). After a certain time period has passed, pump 60 is stopped (ST6), and accordingly three-way cock 61 switches to the state in FIG. 7B to allow pump 60 and press air bag 12 to communicate with each other (ST7). Then, pump 60 operates to supply air into press air bag 12 (ST8). Air bag 12 is thus expanded, causing air bag 11 to pressurize a measurement site (wrist portion) sufficiently to start measurement of blood pressure (ST9). At this time, slow air-release valve 63 opens to gradually discharge air from press air bag 12.

When the measurement of blood pressure is completed, three-way cock 61 switches to the position as shown in FIG. 7C, so that communication is established between pump 60, pressurization air bag 11 and press air bag 12 (ST10). Rapid air-release valve 62 is then opened to discharge air from both air bags 11 and 12 (ST11). Completion of the air release ends the measurement of blood pressure (ST12).

The embodiments above are all applied to the cuffs for the wrist sphygmomanometers. However, they are similarly applicable to a cuff which is wrapped around the arm. I addition, although the press portions are all air bags for press, they may be implemented as a band which is wrapped around a subject region and has an automatic adjustment mechanism for circumferential length. The automatic adjustment mechanism for circumferential length is composed of a gear and a motor, for example, and the motor operates to rotate the gear for adjustment of the circumferential length of the band in order to lengthen or shorten it. When the circumferential length of the band is shortened, pressurization air bag 11 (FIGS. 1 to 4) or press film 16 (FIG. 5) pressurizes the artery. If the band having the automatic circumference adjustment mechanism is employed, this band also selves as band 13 as the attachment unit.

Although the air bag, to and from which air is supplied and discharged, is employed as a fluid bag, the air bag may be any fluid bag to and from which any fluid except the air (gas such as oxygen and carbon dioxide or liquid such as water) is supplied and discharged. In particular, if hydrogen liquid is used, it is necessary to construct a liquid-tight fluid system to prevent leakage of the liquid.

Fourth Embodiment

The fourth embodiment of the present invention is hereinafter described. It is noted that a sphygmomanometer cuff in the fourth embodiment is a modification of the third embodiment, and the description is mainly applied to the modified aspects.

Figure 10A:
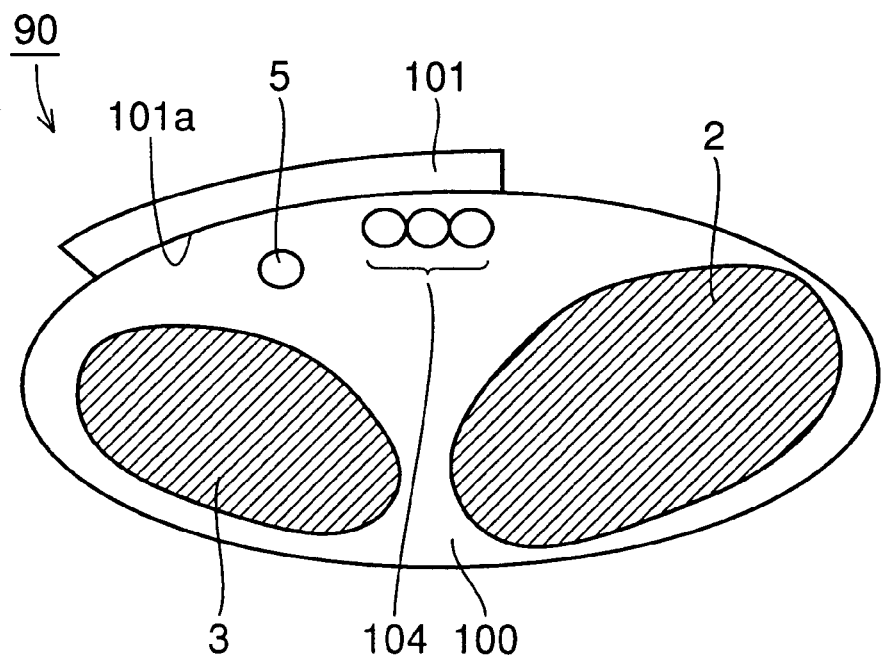
FIGS. 10A and 10B are respectively a schematic cross section and a partially enlarged cross section illustrating a state of a pressurization fluid bag when a sphygmomanometer cuff is attached to a subject region in a further embodiment of the invention.
Figure 10B:
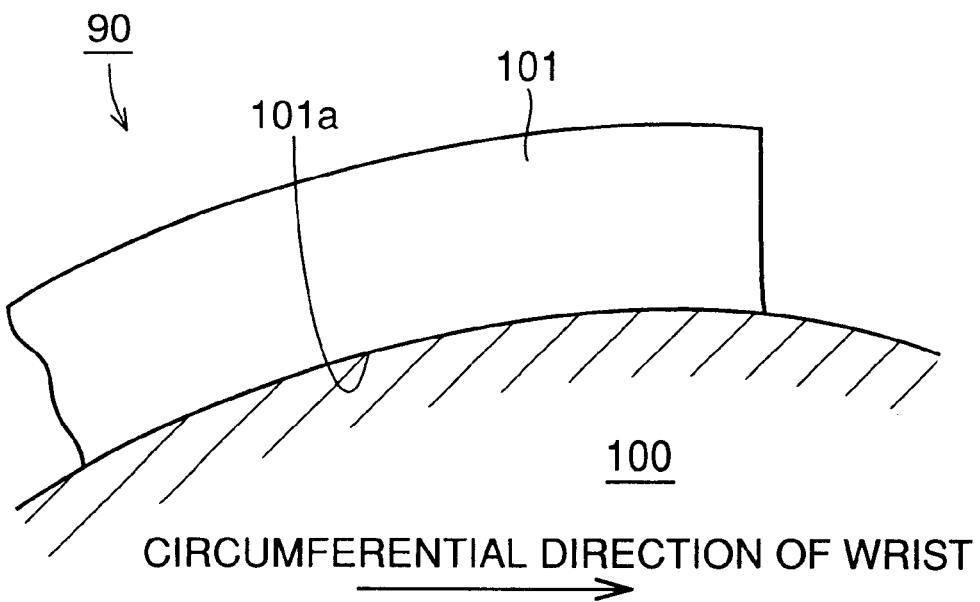

FIGS. 10A and 10B illustrate a state of a pressurization fluid bag of a sphygmomanometer cuff in the fourth embodiment which is attached to a particular region of a living subject. It is noted that only pressurization fluid bag 101 is shown in FIGS. 10A and 10B and other components similar to those in the third embodiment are not shown. Specifically, cuff 90 shown is employed in a wrist sphygmomanometer and constituted of pressurization fluid bag 101 into which a predetermined amount of fluid (air) is supplied so as to pressurize a radial artery 5 of subject region (wrist portion) 100, a fluid bag for press which causes pressurization fluid bag 101 to press wrist portion 100, and a band with a hook-and-loop fastener of a strip-like shape for attaching both bags to wrist portion 100. As shown in FIG. 10A, there is a tendon 104 inside radial artery 5.

Referring to FIG. 10A, pressurization fluid bag 101 of cuff 90 is entirely curved to fit along the surface of subject region 100. In particular, pressurization fluid bag 101 is curved at a radius of curvature corresponding to that of the surface of subject region 100. When cuff 90 having pressurization fluid bag 101 is attached to subject region 100 and the press fluid bag is expanded for measuring blood pressure, a pressurization surface 101a of fluid bag 101 closely fits the surface of subject region 100 without gap as shown in FIG. 10B. The pressure on the artery can thus be detected accurately and blood pressure is accordingly measured with high precision.

Figure 11:
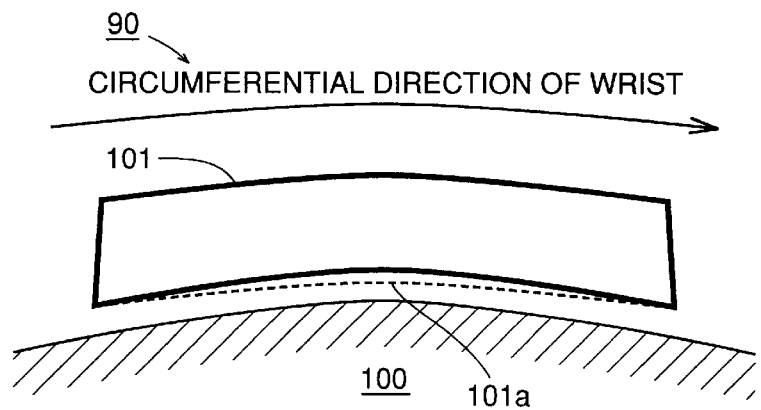
FIG. 11 is a schematic cross sectional view illustrating a modification of the pressurization fluid bag of the cuff shown in FIGS. 10A and 10B.

In a modification shown in FIG. 11, a pressurization surface 101a of a pressurization fluid bag 101 which is entirely curved as described above rises outward relative to the surface around pressurization surface 101a. Since pressurization surface 101a rises outward originally, pressurization surface 101a does not go inside beyond the surface around pressurization surface 101a when the cuff is attached to subject region 100. In this way, pressurization surface 101a surely pressurizes subject region 100 to achieve a higher precision of blood pressure measurement.

Figure 12A:
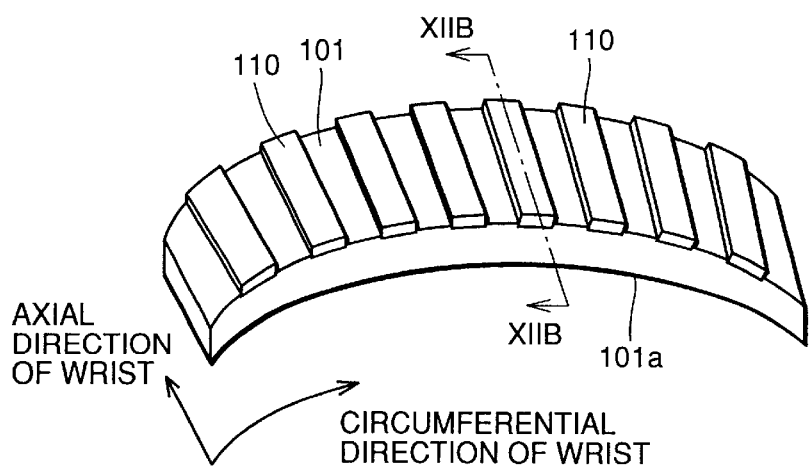
FIGS. 12A and 12B are respectively a perspective view and a cross sectional view along line XIIB—XIIB in FIG. 12A illustrating another modification of the pressurization fluid bag of the cuff.
Figure 12B:
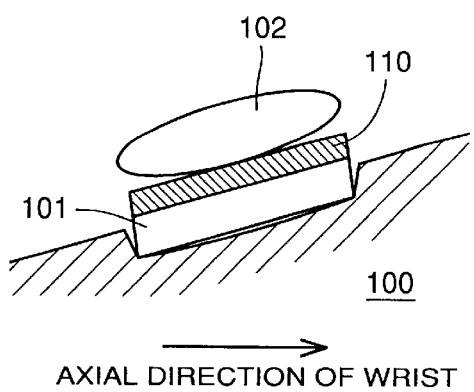

In a modification shown in FIGS. 12A and 12B illustrating a pressurization fluid bag 101 entirely curved as described above, rigid strips 110 extending in the axial direction (direction of the axis of wrist) of a subject region are arranged in the circumferential direction (direction of the circumference of wrist) on the opposite side relative to a pressurization surface 101a (FIG. 12A). Rigid strip 110, as it is "rigid," does not change in shape nor stretch in the axial and circumferential directions of the wrist, and may be formed of any rigid material such as metal and plastic. Pressurization fluid bag 101 has the structure which is easy to change in shape in the circumferential direction of the wrist according to the surface of the subject region, while it does not change in shape in the axial direction of the wrist as rigid strips 110 are provided.

Therefore, as shown in FIG. 12B, when a cuff having pressurization fluid bag 101 is attached to subject region 100 and a press fluid bag 102 is expanded, pressurization fluid bag 101 does not change in shape in the axial direction of the wrist and accordingly presses subject region 100 uniformly over the whole width. Consequently, a more accurate measurement of pressure on the artery is possible.

Figure 13:
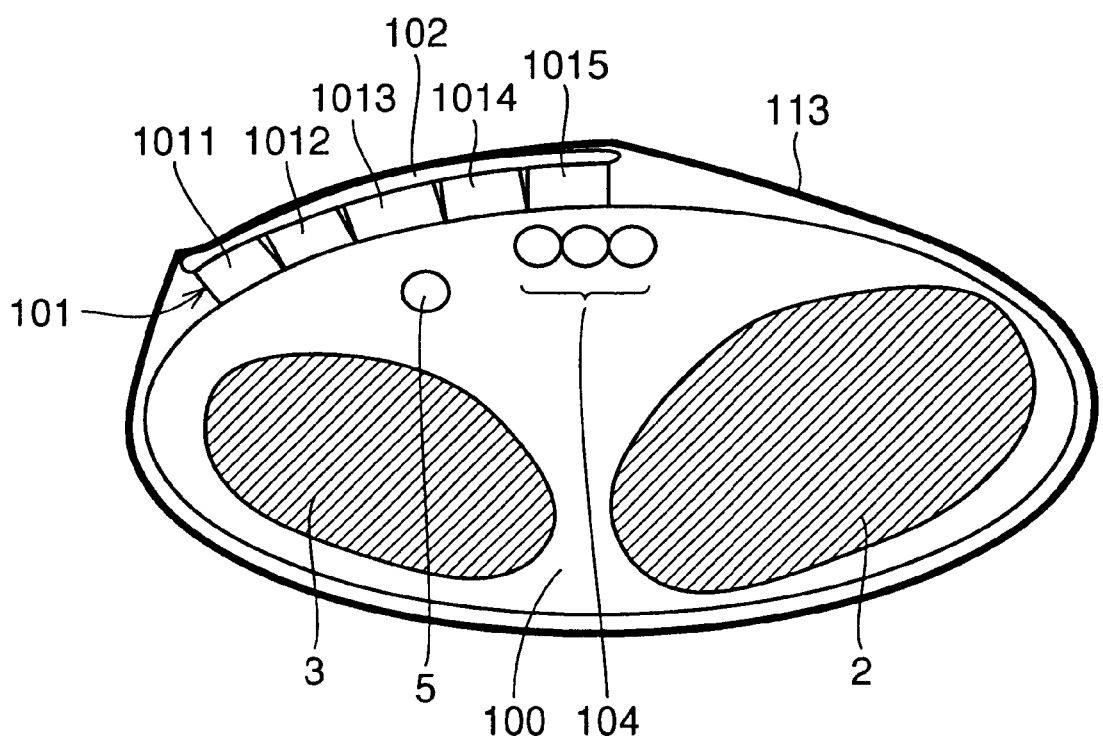
FIG. 13 is a schematic cross sectional view illustrating a sphygmomanometer cuff attached to a subject region in a further modification of the invention.

In a further modification shown in FIG. 13, a pressurization fluid bag 101 is divided into small parts arranged in the circumferential direction of the subject region. Here, fluid bag 101 is formed of five small fluid bags 1011, 1012, 1013, 1014 and 1015 that communicate with each other where fluid (air) is supplied and discharged all together. When a cuff having pressurization fluid bag 101 with divided small parts is attached by a band 113 to subject region 100, fluid bags 1011 to 1015 of pressurization fluid bag 101 individually change in shape according to the shape of subject region 100. Accordingly, pressurization fluid bag 101 suitably fits onto the surface of subject region 100 so that the pressure on artery can correctly be measured.

Figure 14A:
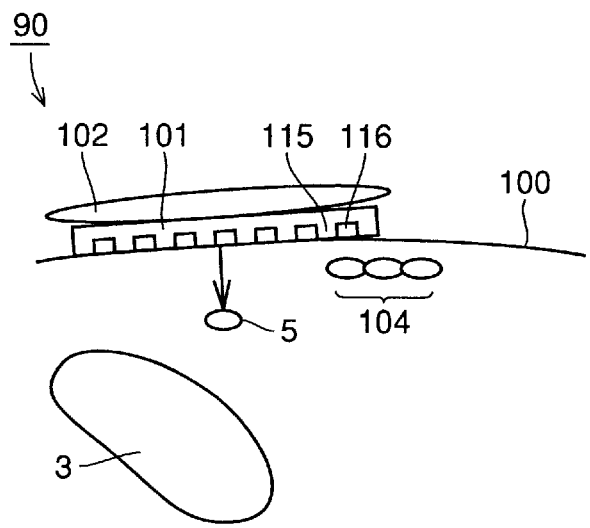
FIGS. 14A to 14C are schematic cross sections illustrating a sphygmomanometer cuff attached to a subject region for measuring blood pressure in a further modification of the invention.
Figure 14B:
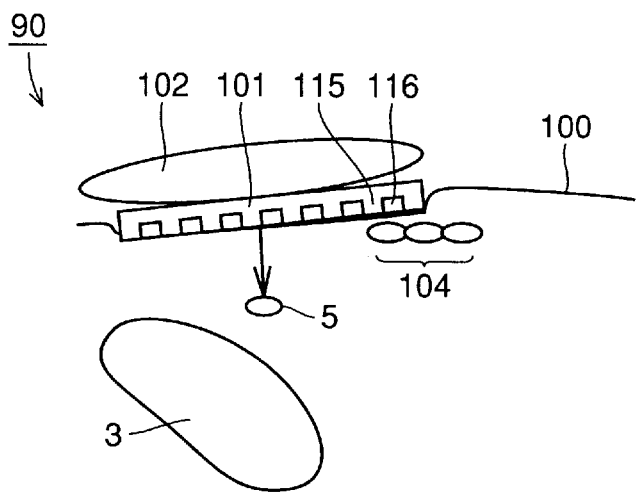
Figure 14C:
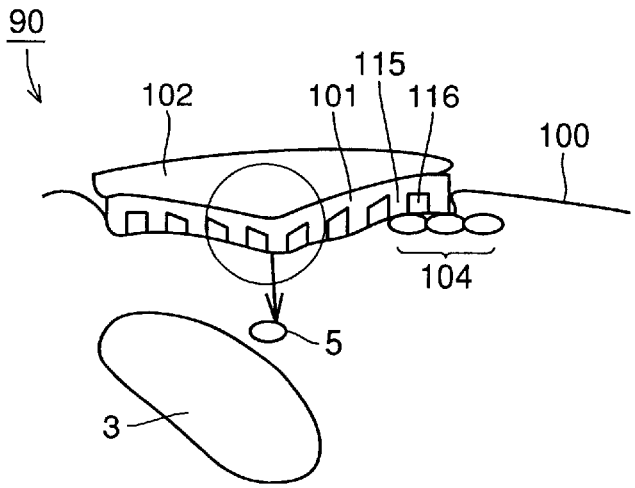

FIGS. 14A to 14C illustrate a sphygmomanometer cuff 90 in a further modification which is attached to a subject region for measurement of blood pressure. A pressurization fluid bag 101 has a wavelike structure with a projection 115 and a depression 116 extending in the axial direction of the subject region. When cuff 90 having pressurization fluid bag 101 is attached to subject region 100 (FIG. 14A) and a press fluid bag 102 is expanded, the portion of fluid bag 101 near a tendon 104 is caught by tendon 104, while the remaining portion moves in the direction in which pressure is exerted (the direction of the arrow) regardless of the caught portion owing to the wavelike structure (FIG. 14B). When press fluid bag 102 is further expanded, the central portion of pressurization fluid bag 101 moves in the direction of pressurization without being influenced by the portion caught by tendon 104 (FIG. 14C). In this way, a radial artery 5 is pressurized surely between pressurization fluid bag 101 and a radius 3 to enable the pressure on the artery to be detected accurately.

Figure 15A:
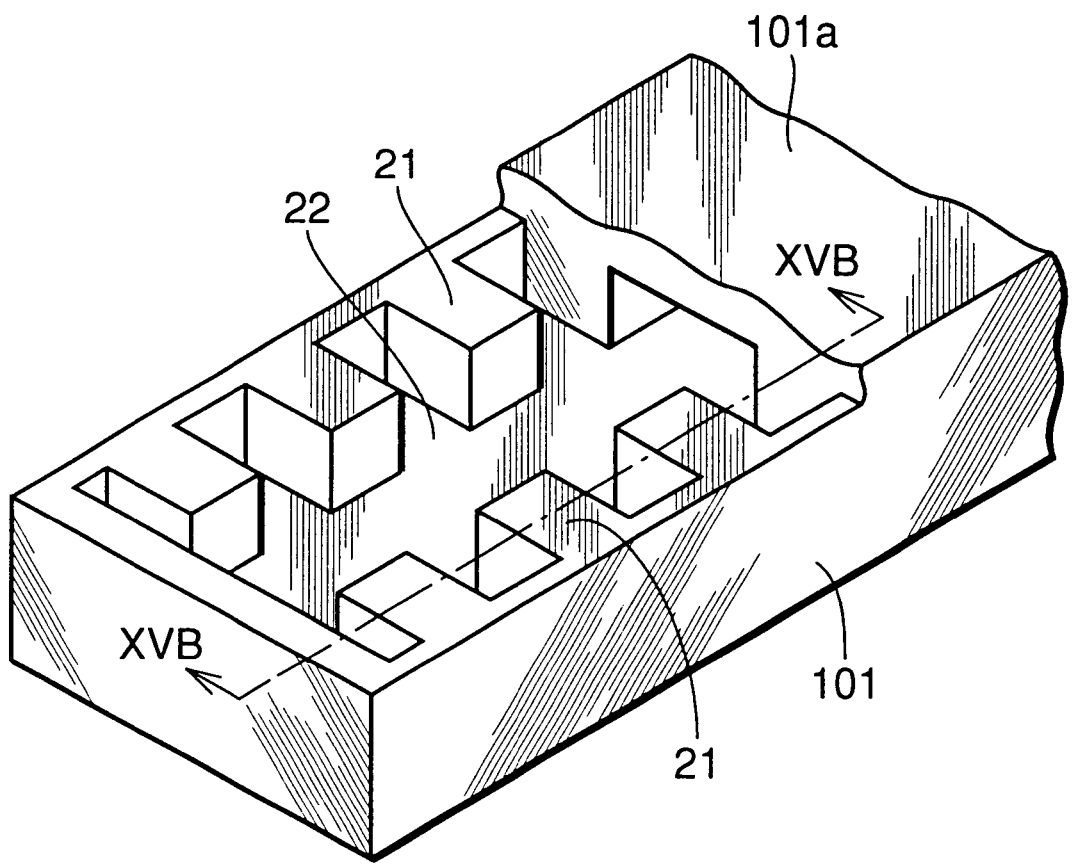
FIGS. 15A and 15B are respectively a partial perspective view illustrating one example of a wavelike structure of the pressurization fluid bag of the cuff and a cross sectional view along line XVB—XVB in FIG. 15A.
Figure 15B:
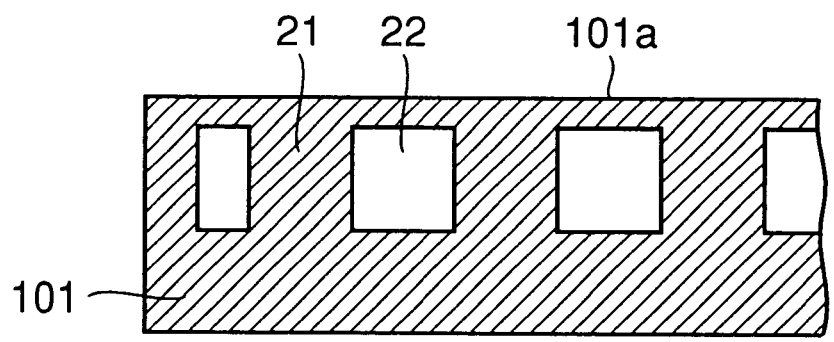

FIGS. 15A and 15B illustrate another wavelike structure of pressurization fluid bag 101. A pressurization fluid bag 101 here has projections 21 shaped like rectangular columns in an internal space 22 where fluid (air) is introduced, and projections 21 are arranged in the circumferential direction of a subject region. This pressurization fluid bag 101 also achieves a similar effect to that illustrated in FIGS. 14A to 14C. Although a pressurization surface 101a is integrated with pressurization fluid bag 101 in FIGS. 15A and 15B, only pressurization surface 101a may be formed as a separate body to be fixed to the main body of fluid bag 101 by adhesive or the like.

Figure 16A:
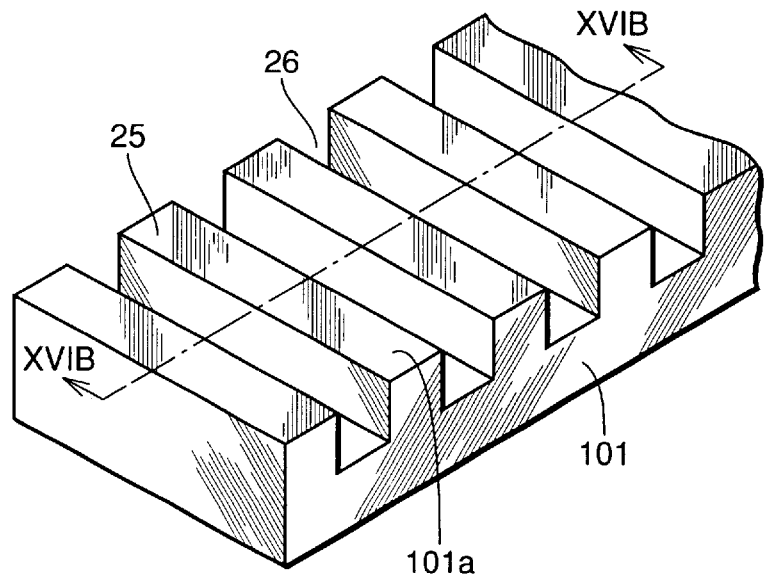
FIGS. 16A and 16B are respectively a partial perspective view illustrating another example of the wavelike structure of the pressurization fluid bag of the cuff and a cross sectional view along line XVIB—XVIB in FIG. 16A.
Figure 16B:
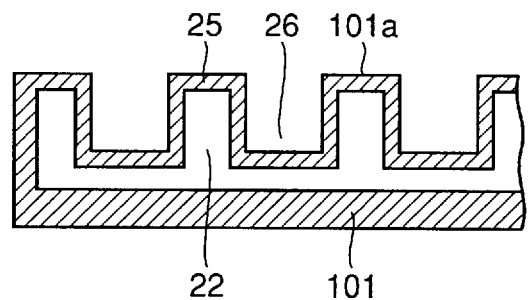

FIGS. 16A and 16B illustrate still another wavelike structure. A pressurization fluid bag 101 here is similar to that shown in FIGS. 14A to 14C in that it has a projection 25 and a depression 26 on a pressurization surface 101a. In this case, pressurization surface 101a also has the wavelike structure, so that pressurization surface 101a is not excessively pulled when pressures is exerted and thus the radial artery can be pressurized more effectively to make a more accurate measurement of the pressure on the artery.

Figure 17:
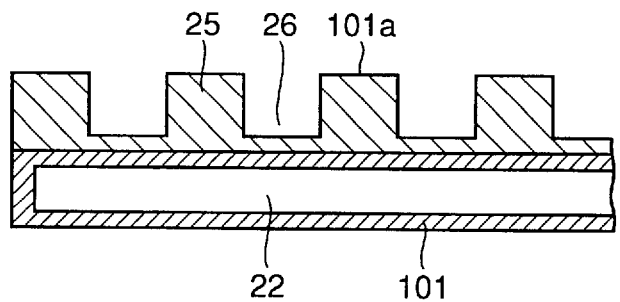
FIG. 17 is a partial cross sectional view illustrating a modification of the pressurization fluid bag in FIG. 16B.

Although projection 25 and depression 26 are integrated with pressurization fluid bag 101 in FIGS. 16A and 16B, a portion having a projection 25 and a depression 26 may be formed separately to be fixed to the main body of fluid bag 101 as shown in FIG. 17. In this case, a space 22 into which fluid is introduced is located in the main body only, while almost the same effect can be obtained.

Figure 18A:
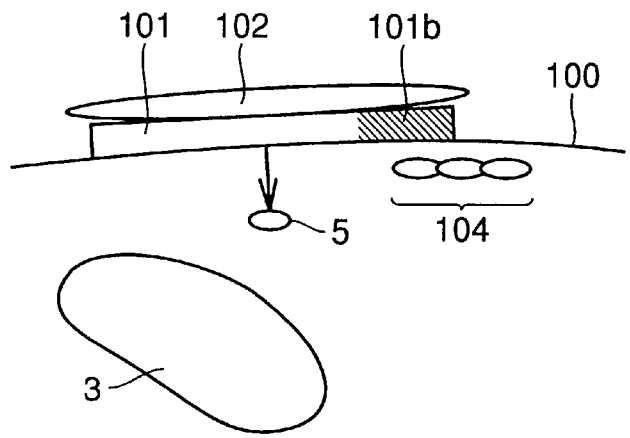
FIGS. 18A to 18C are schematic cross sectional views illustrating a sphygmomanometer cuff attached to a subject region to measure blood pressure in a further modification of the invention.
Figure 18B:
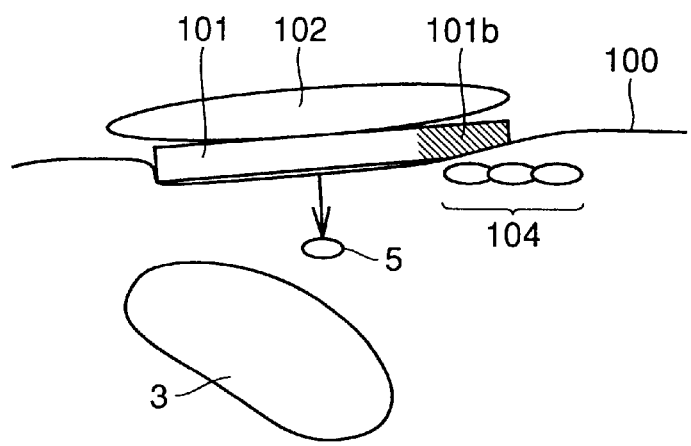
Figure 18C:
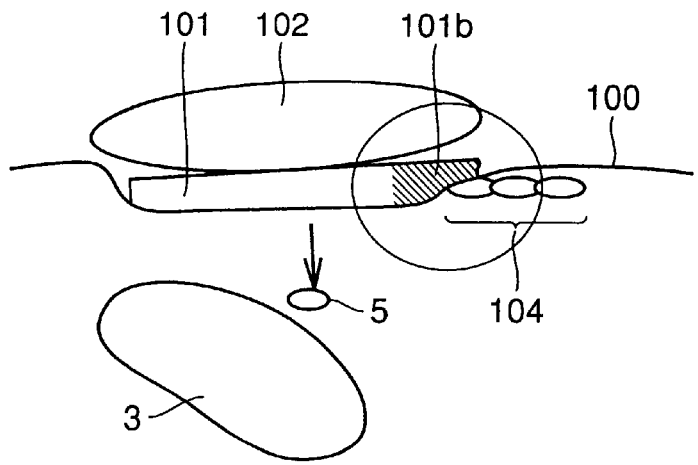

FIGS. 18A to 18C illustrate a sphygmomanometer cuff attached to a subject region for measurement of blood pressure in a further modification of the invention. A pressurization fluid bag 101 here has a portion 101b (the portion to be associated with a tendon 104 in this example) extending in the axial direction of the subject region that has a hardness different from that of the remaining portion. Specifically, the elasticity of portion 101b is higher than that of the remaining portion and therefore portion 101b is more flexible compared with the remaining portion.

When a cuff having pressurization fluid bag 101 is attached to subject region 100 (FIG. 18A) and a press fluid bag 102 is expanded, portion 101b of fluid bag 101 touches tendon 104 and significantly shrinks (FIG. 18B). When press fluid bag 102 is further expanded, only the portion 101b of pressurization fluid bag 101 shrinks greatly and the remaining portion pressurizes a radial artery 5 between itself and a radius 3 without being influenced by portion 101b (FIG. 18C). In this way, a correct detection of the pressure on the artery is possible.

Figure 19:
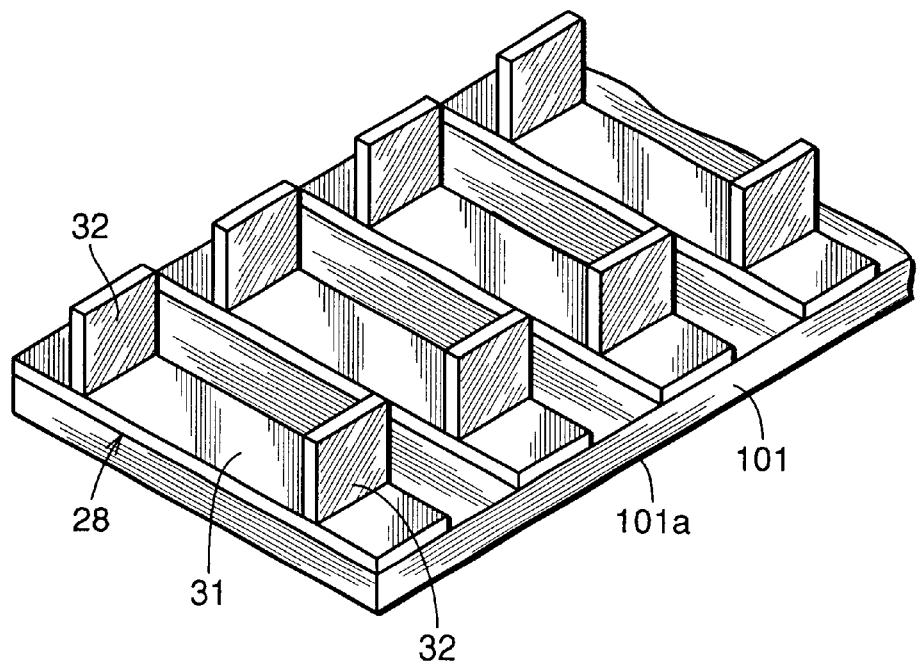
FIG. 19 is a partial perspective view illustrating a pressurization fluid bag of a sphygmomanometer cuff in a further modification of the invention.
Figure 20:
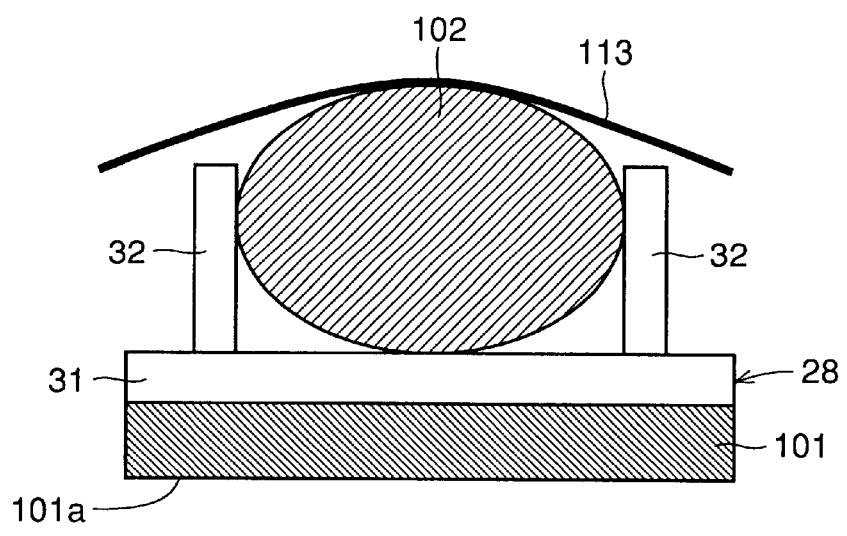
FIG. 20 is a schematic cross sectional view illustrating the cuff having the pressurization fluid bag in FIG. 19 which is attached to a subject region.

FIG. 19 illustrates a pressurization fluid bag of a sphygmomanometer cuff in a further modification of the invention, and FIG. 20 illustrates the cuff having the pressurization fluid bag shown in FIG. 19. Pressurization fluid bag 101 has a restraint tool 28 which deters a press fluid bag 102 from expanding in the axial direction of a subject region (wrist portion), placed on the other side of a pressurization surface 101a. Restraint tools 28 are each formed of a flat plate 31 attached to pressurization fluid bag 101 and a pair of walls 32 placed to stand on both sides of plate 31 and tools 28 are spaced apart in the circumferential direction of the wrist. Press fluid bag 102 is placed between walls 32 of restraint tools 28.

Figure 21A:
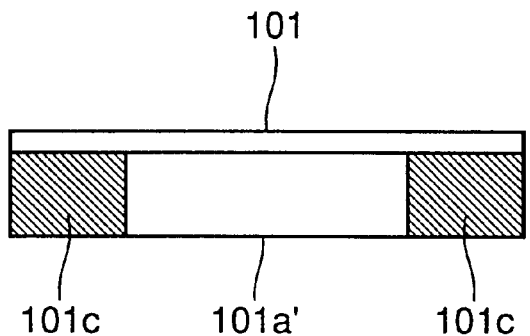
FIGS. 21A and 21B are respectively a schematic cross sectional view of a pressurization fluid bag of a sphygmomanometer cuff in a further modification and a schematic cross sectional view illustrating a state of the pressurization fluid bag when the cuff is attached to a subject region.
Figure 21B:
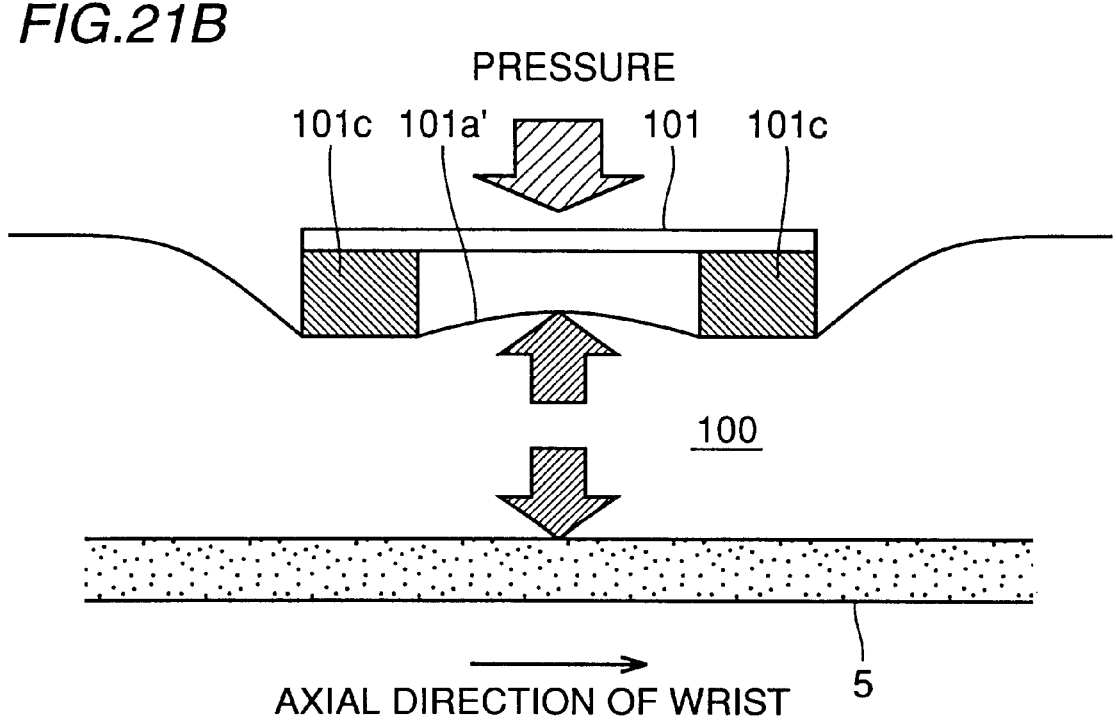

When press fluid bag 102 of the cuff having pressurization fluid bag 101 with restraint tools 28 is expanded as shown in FIG. 20, walls 32 of restraint tools 28 prevent fluid bag 102 from expanding in the axial direction of the wrist so that the press force generated by expansion of press fluid bag 102 is efficiently transmitted to pressurization fluid bag 101 and accordingly the rate of transmission of the pressurization force enhances. In this case, plate 31 of restraint tool 28 exhibits the similar effect to that of rigid body 110 shown in FIGS. 12A and 12B FIGS. 21A and 21B illustrate a pressurization fluid bag of a sphygmomanometer cuff in a further modification. Pressurization fluid bag 101 here includes a pressurization surface 101a' which is more elastic than the subject region, and portions 101c having a compression displacement relative to the pressure from the subject region that is smaller than the compression displacement of fluid inside pressurization surface 101a'. Portions 101c are provided on both sides of pressurization surface 101a' in the axial direction of the wrist. Referring to FIG. 21B, when pressure is exerted on the cuff having this pressurization fluid bag 101, pressurization surface 101a' of pressurization fluid bag 101 is pushed by subject region 100 to be displaced inward, while portions 101c except pressurization surface 101a' exhibit smaller displacement than that of pressurization surface 101a'. Consequently, the internal pressure of pressurization fluid bag 101 and the pressure on an artery 5 become almost equal to each other so that the pressure on the artery can be detected correctly.

Figure 22A:
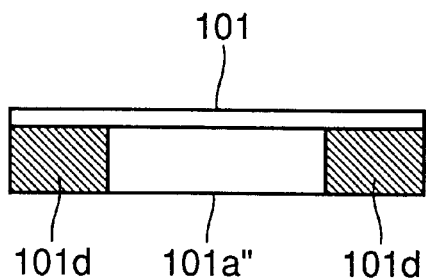
FIG. 22A is a schematic cross sectional view of a pressurization fluid bag of a sphygmomanometer cuff in a further modification and FIG. 22B is a schematic cross sectional view illustrating a state of the pressurization fluid bag when the cuff is attached to a subject region.
Figure 22B:
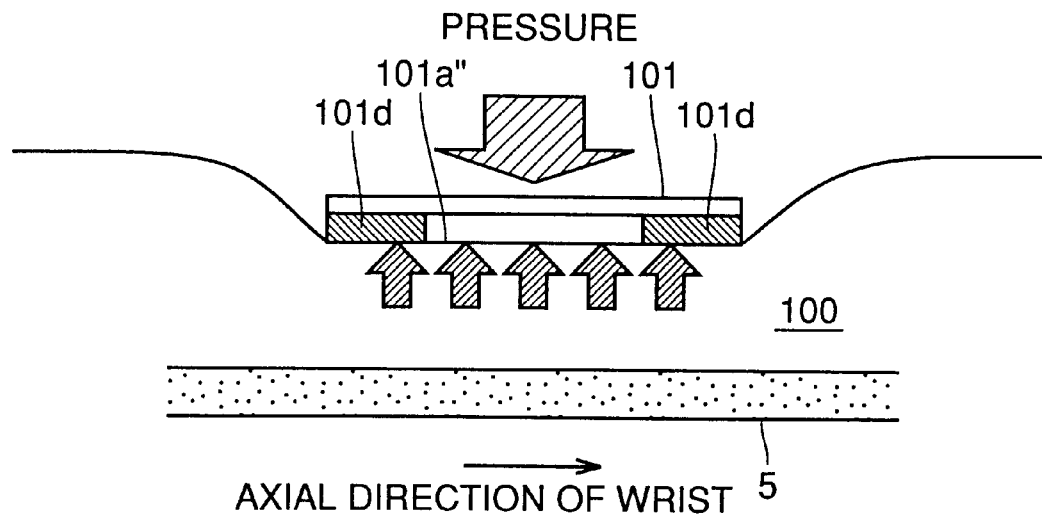

FIGS. 22A and 22B illustrate a pressurization fluid bag of a sphygmomanometer cuff in a further modification. Pressurization fluid bag 101 here includes a pressurization surface 101a" which is less elastic than the subject region, and portions 101d having a compression displacement relative to the pressure from the subject region that is greater than the compression displacement of the fluid inside pressurization surface 101a". Portions 101d are placed on both sides of pressurization surface 101a" in the axial direction of the wrist. When pressure is exerted on the cuff having this pressurization fluid bag 101 as shown in FIG. 22B, pressurization surface 101a" of pressurization fluid bag 101 is hardly displaced while portions 101d except pressurization surface 101a" are displaced according to the pressurization force. As a result, the distribution of the pressurization force over pressurization surface 101a" of pressurization fluid bag 101 becomes uniform, i.e. the uniform pressurization force is exerted regardless of the position of pressurization surface 101a" and accordingly the pressure on the artery can be measured correctly.

Figure 23A:
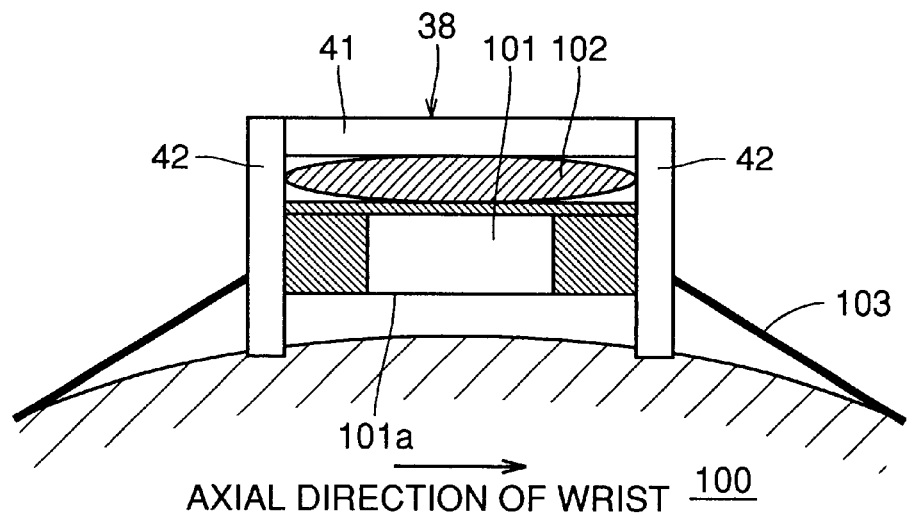
FIGS. 23A and 23B are schematic cross sectional views illustrating a sphygmomanometer cuff attached to a subject region in a further modification, showing respectively the states before measurement and at the time of measurement.
Figure 23B:
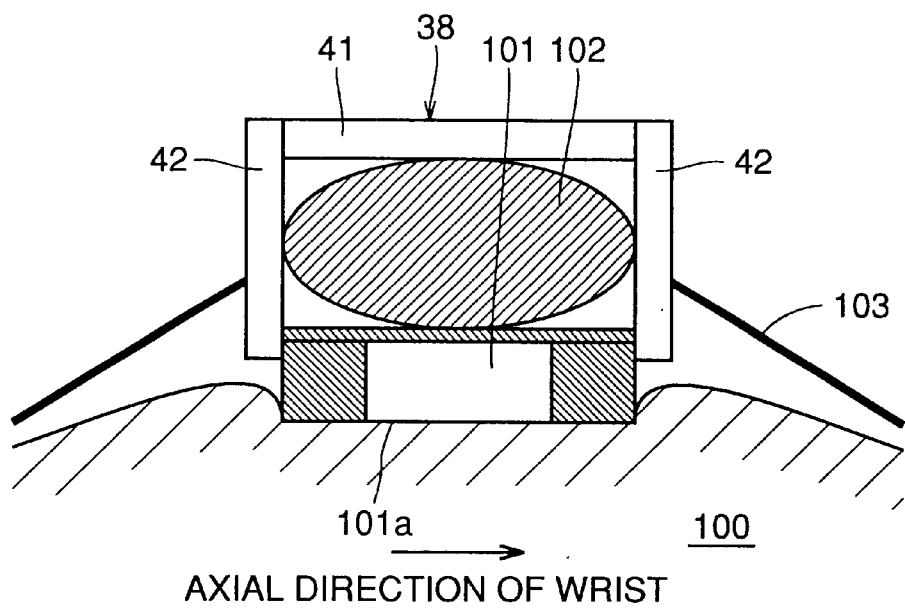

FIGS. 23A and 23B illustrate a sphygmomanometer cuff attached to a subject region in a further modification. This cuff has a cover 38 for preventing a pressurization fluid bag 101 from being subjected to the pressure from subject region 100 or any external pressure when the cuff is attached to subject region 100. Cover 38 is formed of a back wall 41 located outside a press fluid bag 102 and side walls 42 located on both sides of pressurization fluid bag 101 and press fluid bag 102 in the axial direction of the wrist, and the cuff is thus covered with cover 38 in the axial and circumferential directions of the wrist. Within cover 38, pressurization fluid bag 101 and press fluid bag 102 can be displaced in the direction of pressure. When press fluid bag 102 is not inflated, a pressurization surface 101a of pressurization fluid bag 101 is located inside relative to the leading end of side wall 42 of cover 38.

When the cuff having cover 38 is attached to subject region 100, pressurization fluid bag 101 stands located within cover 38. The leading end of side wall 42 of cover 38 is pressed by subject region 100 while pressurization surface 101a of pressurization fluid bag 101 is placed inside relative to the leading end of side wall 42. Therefore, pressurization fluid bag 101 is never subjected to the pressure from subject region 100 as a counter action nor to any external pressure (e.g. pulling force of cover 38). In this way, zero point of the pressure can be adjusted precisely with the cuff attached as it is, and a correct measurement of blood pressure is thus possible.

When the measurement is started after adjustment of the zero point, pressurization fluid bag 101 is pressed by expanded press fluid bag 102 to be displaced toward subject region 100 and thus project from the leading end of side wall 42 of cover 38. Accordingly, pressurization surface 101a pressurizes subject region 100.

Figure 24A:
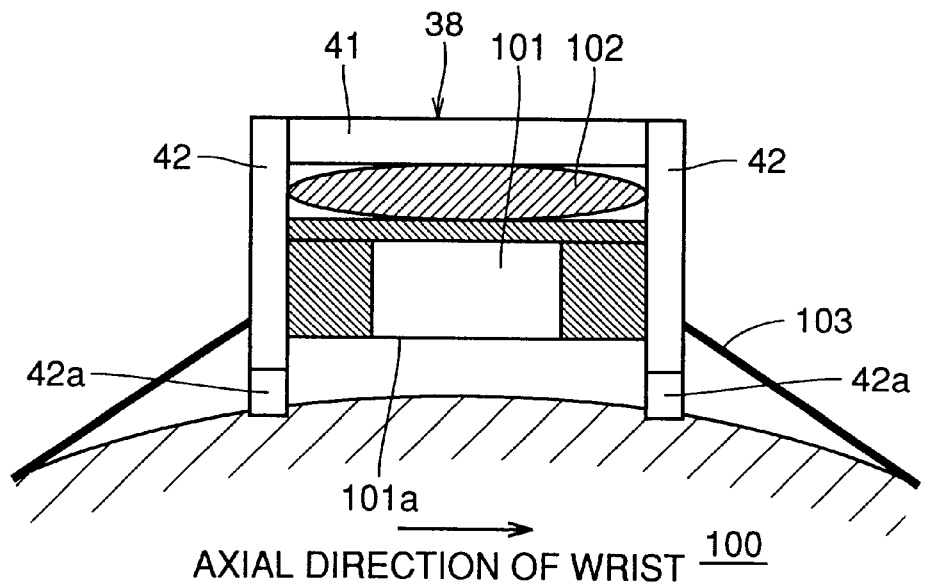
FIGS. 24A and 24B are schematic cross sectional views illustrating a modification of the cuff shown in FIGS. 23A and 23B respectively showing the states before measurement and at the time of measurement.
Figure 24B:
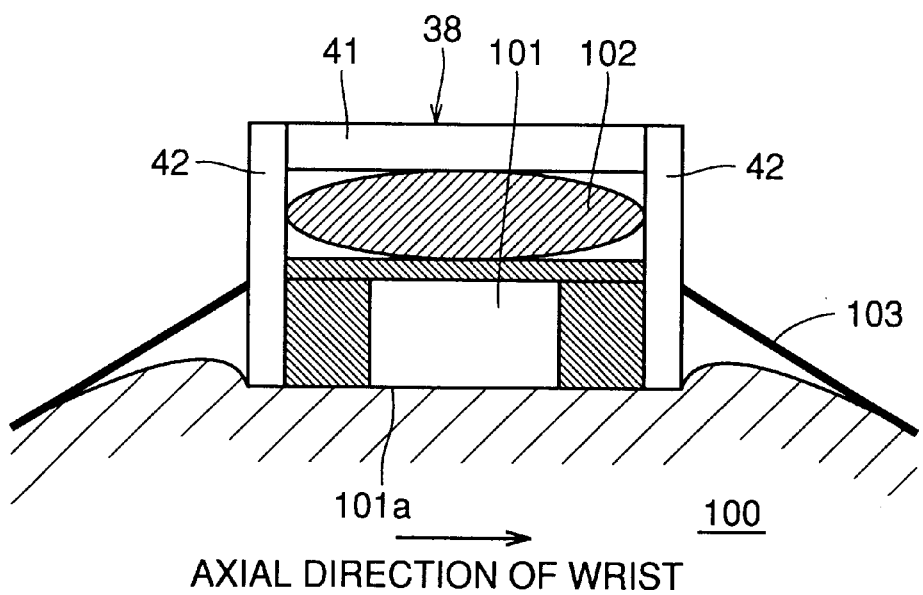

Pressurization fluid bag 101 projects from cover 38 when measurement is done as shown in FIGS. 23A and 23B. FIGS. 24A and 24B illustrate another manner in which a leading end 42a of a side wall 42 of a cover 38 is extensible. Specifically, leading end 42a can slide into and out of side wall 42 such that it enters side wall 42 only when the measurement is done and it projects at other times.

When the cuff is attached to subject region 100 first, pressurization fluid bag 101 is inside cover 38 (FIG. 24A). Leading end 42a of side wall 42 enters side wall 42 simultaneously with start of measurement and accordingly pressurization surface 101a of pressurization fluid bag 100 contacts subject region 100 (FIG. 24B). After this, a press fluid bag 102 is inflated to press pressurization fluid bag 101 and accordingly cause pressurization surface 101a to pressurize subject region 100.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A sphygmomanometer cuff comprising:
   a pressurization fluid bag into or in which a predetermined amount of fluid is supplied or confined and which is connected to a pressure sensor;
   a press portion into which a predetermined amount of fluid is supplied for causing said pressurization fluid bag to press a subject region; and
   an attachment unit for attaching said pressurization fluid bag and said press portion to the subject region,
   wherein said press portion is formed of an intervening member placed outside said pressurization fluid bag and a fluid bag for press placed outside said intervening member.

2. The sphygmomanometer cuff according to claim 2, wherein said pressurization fluid bag is positioned relative to an artery by said intervening member.

3. The sphygmomanometer cuff according to claim 2, wherein said pressurization fluid bag is formed of a fluid introduction member having a space into which fluid is supplied and a press film attached to said fluid introduction member so as to seal the space.

4. A sphygmomanometer cuff comprising:
   a pressurization fluid bag into or in which a predetermined amount of fluid is supplied or confined and which is connected to a pressure sensor, said pressurization fluid bag being curved to conform to a surface of a subject region;
   a press portion into which a predetermined amount of fluid is supplied to permit said pressurization fluid bag to press the subject region; and
   an attachment unit for attaching said pressurization fluid bag and said press portion to the subject region, wherein said pressurization fluid bag has rigid strips extending in axial direction of the subject region and arranged in circumferential direction of the subject region on opposite side of a pressurization surface of said pressurization fluid bag.

5. A sphygmomanometer cuff comprising:
   a pressurization fluid bag into or in which a predetermined amount of fluid is supplied or confined and which is connected to a pressure sensor, said pressurization fluid bag being divided into small parts which are arranged in circumferential direction of a subject region;
   a press portion into which a predetermined amount of fluid is supplied to permit said pressurization fluid bag to press the subject region; and
   an attachment unit configured to attach said pressurization fluid bag and said press portion to the subject region.

6. A sphygmomanometer cuff comprising:
   a pressurization fluid bag into or in which a predetermined amount of fluid is supplied or confined and which is connected to a pressure sensor, said pressurization fluid bag having a wavelike structure with projection and depression extending in axial direction of a subject region;
   a press portion into which a predetermined amount of fluid is supplied to permit said pressurization fluid bag to press the subject region; and
   an attachment unit configured to attach said pressurization fluid bag and said press portion to the subject region.

7. The sphygmomanometer cuff according to claim 6, wherein
   said pressurization fluid bag has a pressurization surface of a wavelike shape.

8. A sphygmomanometer cuff comprising:
   a pressurization fluid bag into or in which a predetermined amount of fluid is supplied or confined and which is connected to a pressure sensor, said pressurization fluid bag having a portion extending in axial direction of a subject region with its hardness different from that of a remaining portion;
   a press portion into which a predetermined amount of fluid is supplied to permit said pressurization fluid bag to press the subject region; and
   an attachment unit configured to attach said pressurization fluid bag and said press portion to the subject region.

9. A sphygmomanometer cuff comprising:
   a pressurization fluid bag into or in which a predetermined amount of fluid is supplied or confined and which is connected to a pressure sensor;
   a press portion into which a predetermined amount of fluid is supplied for causing said pressurization fluid bag to press a subject region; and
   an attachment unit for attaching said pressurization fluid bag and said press portion to the subject region, wherein
   said press portion is a fluid bag for press which is placed opposite to a pressurization surface of said pressurization fluid bag and expanded and shrunk by fluid which is supplied into or discharged from said press portion, and
   said pressurization fluid bag has a restraint tool placed opposite to the pressurization surface for deterring said fluid bag for press from bulging in axial direction of the subject region.

10. A sphygmomanometer cuff comprising:

a pressurization fluid bag into or in which a predetermined amount of fluid is supplied or confined and which is connected to a pressure sensor;

a press portion into which a predetermined amount of fluid is supplied for causing said pressurization fluid bag to press a subject region; and an attachment unit for attaching said pressurization fluid bag and said press portion to the subject region, wherein said pressurization fluid bag has a pressurization surface which is more elastic than the subject region and a portion having a compression displacement relative to pressure from the subject region that is smaller than compression displacement of fluid inside said pressurization surface.

11. A sphygmomanometer cuff comprising:

a pressurization fluid bag into or in which a predetermined amount of fluid is supplied or confined and which is connected to a pressure sensor;

a press portion into which a predetermined amount of fluid is supplied for causing said pressurization fluid bag to press a subject region; and an attachment unit for attaching said pressurization fluid bag and said press portion to the subject region, wherein said pressurization fluid bag has a pressurization surface which is less elastic than the subject region and a portion having a compression displacement relative to pressure from the subject region that is greater than compression displacement of fluid inside said pressurization surface.

12. A sphygmomanometer cuff comprising:

a pressurization fluid bag into or in which a predetermined amount of fluid is supplied or confined and which is connected to a pressure sensor;

a press portion into which a predetermined amount of fluid is supplied for causing said pressurization fluid bag to press a subject region; and an attachment unit for attaching said pressurization fluid bag and said press portion to the subject region, wherein said sphygmomanometer cuff further comprises a cover for preventing said pressurization fluid bag from being subjected to pressure from the subject region and any external pressure when said cuff is attached to the subject region.

13. The sphygmomanometer cuff according to claim 17, wherein said cover has a pair of extensible walls extending in circumferential direction of the subject region, said walls stretching to separate said pressurization fluid bag from the subject region when said cuff is attached to the subject region and shortening to cause said pressurization fluid bag to touch the subject region when measurement is done.

* * * * *

UNITED STATES PATENT AND TRADEMARK OFFICE
CERTIFICATE OF CORRECTION

PATENT NO.    : 6,336,901 B1
DATED         : January 8, 2002
INVENTOR(S)   : Kazunobu Itonaga et al.

It is certified that error appears in the above-identified patent and that said Letters Patent is hereby corrected as shown below:

<u>Title page,</u>
Item [73], Assignee, change the address from "Tokyo" to -- Kyoto --.

<u>Column 13,</u>
Line 48, change "claim 2" to -- claim 1 --.
Line 49, before "positioned", insert -- adapted to --.
Line 51, change "claim 2" to -- claim 1 --.

<u>Column 16,</u>
Line 20, change "claim 17" to -- claim 12 --.

Signed and Sealed this

Twenty-seventh Day of August, 2002

*Attest:*

*Attesting Officer*

JAMES E. ROGAN
*Director of the United States Patent and Trademark Office*